(12) United States Patent
Kim et al.

(10) Patent No.: US 8,834,906 B2
(45) Date of Patent: Sep. 16, 2014

(54) COLOR CAPSULE COMPOSITION FOR COSMETICS, PREPARATION METHOD THEREOF AND COSMETIC FORMULATION COMPRISING THE SAME

(75) Inventors: Chul-Hwan Kim, Daejeon (KR); Tae-Sung Ko, Seoul (KR); Han-Joon Kim, Daejeon (KR); Choa-Jin Kim, Daejeon (KR); Jong-Hyun Choi, Chungchongnamdo (KR); Chang-Hun Ji, Daejeon (KR)

(73) Assignee: Biogenics, Inc., Daejeon (KR)

( * ) Notice: Subject to any disclaimer, the term of this patent is extended or adjusted under 35 U.S.C. 154(b) by 53 days.

(21) Appl. No.: 13/003,781

(22) PCT Filed: May 28, 2010

(86) PCT No.: PCT/KR2010/003391
§ 371 (c)(1),
(2), (4) Date: Jan. 12, 2011

(87) PCT Pub. No.: WO2011/027960
PCT Pub. Date: Mar. 10, 2011

(65) Prior Publication Data
US 2011/0165208 A1  Jul. 7, 2011

(30) Foreign Application Priority Data

Sep. 2, 2009 (KR) .................. 10-2009-0082647

(51) Int. Cl.
| | |
|---|---|
| *A61K 8/02* | (2006.01) |
| *A61K 9/48* | (2006.01) |
| *B29B 9/00* | (2006.01) |
| *A61K 8/11* | (2006.01) |
| *C09B 67/02* | (2006.01) |
| *A61Q 1/02* | (2006.01) |
| *A61K 8/19* | (2006.01) |
| *A61K 8/85* | (2006.01) |

(52) U.S. Cl.
CPC .............. *A61K 8/11* (2013.01); *C09B 67/0097* (2013.01); *A61K 2800/651* (2013.01); *A61K 8/0283* (2013.01); *A61Q 1/02* (2013.01); *A61K 8/19* (2013.01); *A61K 8/85* (2013.01)
USPC ............................ 424/401; 424/451; 264/7

(58) Field of Classification Search
None
See application file for complete search history.

(56) References Cited

U.S. PATENT DOCUMENTS

| | | | | |
|---|---|---|---|---|
| 4,623,588 | A * | 11/1986 | Nuwayser et al. ........ | 428/402.24 |
| 6,548,170 | B2 * | 4/2003 | Perrier et al. ................ | 428/402 |
| 2006/0051425 | A1 * | 3/2006 | Kvitnitsky et al. .......... | 424/490 |
| 2011/0147965 | A1 * | 6/2011 | Mistry et al. ..................... | 264/7 |

FOREIGN PATENT DOCUMENTS

| | | |
|---|---|---|
| EP | 1205843 | 5/2002 |
| JP | 06-271458 | 9/1994 |
| JP | 08-134374 | 5/1996 |
| KR | 1020050084212 | 8/2005 |

OTHER PUBLICATIONS

Wan et al. "Plasticizers and their effects on microencapsulation process by spray-drying in an aqueous system", Journal of Microencapsulation, 9(1), 1992, pp. 53-62.*
Uniform definition, http://www.merriam-webster.com/dictionary/uniform, accessed Jan. 29, 2013.*

* cited by examiner

*Primary Examiner* — Daniel Sullivan
*Assistant Examiner* — Melissa Javier
(74) *Attorney, Agent, or Firm* — IPLA P.A.; James E. Bame

(57) ABSTRACT

Disclosed herein are a color capsule composition, which contains a polymer and a plasticizer swelling the polymer so as to allow the capsule particles to easily break and in which the capsule particles have a porous structure that boosts the effects thereof, and a method for preparing the color capsule composition. The preparation method comprises: uniformly mixing a color pigment, a plasticizer and a polymer in a first solvent to produce a first mixture solution; spray-drying the first mixture solution to produce core particles in which the color pigment is covered by the polymer; uniformly mixing the obtained core particles, a functional pigment and a second solvent to produce a second mixture solution; and spray-drying the second mixture solution to produce in which a coating layer of the functional pigment is formed on the outer surface of the polymer.

8 Claims, 8 Drawing Sheets

Change in hardness of particles according to change in content of plasticizer in Examples 31 to 57 (polyester content : 6.75%)

Change in hardness of particles according to change in content of polyester in Examples 31 to 57 (plasticizer content : 2.25%)

Change in hardness of particles according to change in content of fatty acid in Examples 58 to 63

Change in hardness of particles according to change in content of plasticizer in Examples 64 to 90 (polyaminomethacrylate content : 6.75%)

Change in hardness of particles according to change in content of polyaminomethacrylate in Examples 64 to 90 (plasticizer content : 2.25%)

Change in hardness of particles according to change in content of plasticizer in Examples 91 to 117 (polyester emulsion content : 6.75%)

Change in hardness of particles according to change in content of polyester emulsion in Examples 91 to 117 (plasticizer content: 2.25%)

change in hardness of particles according to change in content of plasticizer in Examples 118 to 144 (polyvinylpyrrolidone content: 6.75%)

Change in hardness of particles according to change in content of polyvinylpyrrolidone in Examples 118 to 144 (plasticizer content : 2.25%)

Change in hardness of particles according to change in content of plasticizer in Examples 145 to 171 (hydroxymethylcellulose content : 6.75%)

Change in hardness of particles according to change in content of hydroxypropylmethylcellulose in Examples 145 to 171 (plasticizer content : 2.25%)

Change in hardness of particles according to change in content of plasticizer in Examples 172 to 198 (shellac content : 6.75%)

Change in hardness of particles according to change in content of shellac in Examples 172 to 198 (plasticizer content : 2.25%)

Change in covering power according to change in content of inorganic coating layer in Examples 226 to 242

COLOR CAPSULE COMPOSITION FOR COSMETICS, PREPARATION METHOD THEREOF AND COSMETIC FORMULATION COMPRISING THE SAME

BACKGROUND OF THE INVENTION

1. Field of the Invention

The present invention relates to a color capsule composition, which contains a polymer and a plasticizer swelling the polymer so as to allow the capsule particles to easily break and in which the capsule particles have a porous structure that boosts the effects thereof, and a method for preparing the color capsule composition.

2. Description of the Prior Art

In conventional methods for preparing color cosmetic particles, coacervation, phase separation or modified encapsulation methods are used to form a structure, which resists swelling or some degree of external force and easily breaks under a certain formulation.

In these methods, the process steps are very complicated and it is difficult to control the particle size. In addition, due to the process characteristics, it is not easy to control the skin covering power of capsules.

Also, in most of these methods, granulation or encapsulation is performed using a wet process, and washing and filtration processes are repeated several times to remove the remaining organic solvent or impurities, thus generating a large amount of wastewater.

Accordingly, a large amount of wastewater is necessarily generated, resulting in an increase in the production cost.

SUMMARY OF THE INVENTION

Accordingly, the present invention has been made in view of the problems occurring in the prior art, and it is an object of the present invention to provide a color capsule composition, which contains a polymer and a plasticizer swelling the polymer so as to allow the capsule particles to easily break and in which the capsule particles have a porous structure that boosts the effects thereof, and a method for preparing the color capsule composition.

Another object of the present invention is to provide a color capsule composition for cosmetics having a core-shell structure and exhibiting skin covering power, which is prepared by preparing core particles made of a polymer surrounding a color pigment, and coating the core particles with a functional pigment having increased covering power, and a method for preparing the color capsule composition.

Still another object of the present invention is to provide a method for preparing a color capsule composition for cosmetics, in which a spray dryer is used to produce micro-size core particles or capsule particles such that the generation of wastewater and the discharge of a volatile solvent can be prevented, and a color capsule composition prepared thereby.

Still another aspect of the present invention is to provide a method for preparing a color capsule composition for cosmetics, in which no surfactant is used such that the physical properties of the final product can be easily controlled and the number of additional process steps can be reduced, and a color capsule composition prepared thereby.

Still another aspect of the present invention is to provide an W/O emulsion formulation, an W/S emulsion formulation and an O/W emulsion formulation using the color pigment-containing capsules.

To achieve the above objects, the present invention provides a color capsule composition for cosmetics prepared by uniformly mixing a color pigment, a plasticizer and a polymer in a first solvent to make a mixture, drying the mixture to make core particles, and uniformly mixing the core particles, a functional pigment and a second solvent.

Preferably, the polymer, the color pigment and the plasticizer are used in amounts of 5-15 wt %, 70-90 wt % and 5-15 wt %, respectively, based on the total weight of the polymer, the color pigment and the plasticizer, and the core particles and the functional pigment are used in amounts of 80-40 wt % and 20-60 wt %, respectively, based on the total weight of the core particles and the functional pigment.

The present invention also provides a method for preparing a color capsule composition for cosmetics, the method comprising the steps of: uniformly mixing a color pigment, a plasticizer and a polymer in a first solvent to produce a first mixture solution; spray-drying the first mixture solution to produce core particles in which the color pigment is covered by the polymer; uniformly mixing the obtained core particles, a functional pigment and a second solvent to produce a second mixture solution; and spray-drying the second mixture solution to produce in which a coating layer of the functional pigment is formed on the outer surface of the polymer.

Preferably, fatty acid is further added to the first mixture solution.

Preferably, the polymer is any one selected from the group consisting of polyester, a polyester emulsion, polyaminomethacrylate, polyvinylpyrrolidone, hydroxypropylmethylcellulose, and shellac.

Preferably, the plasticizer is any one selected from the group consisting of 1,3-butanediol, polyethylene glycol, and dipropylene glycol.

Preferably, the color pigment is any one selected from the group consisting of iron oxide pigments, organic pigments, lake dyes, and natural pigments.

Preferably, the first and second solvents are any one selected from the group consisting of acetone, ethanol and distilled water.

Preferably, the functional pigment is any one selected from the group consisting of titanium dioxide, zinc oxide, boron nitride, talc, mica, and a mixture of two or more thereof.

Preferably, in the step of producing the first mixture solution, 4.5 g of the polymer, 39.15 g of the color pigment and 2.25 g of the plasticizer are used, and in the step of producing the second mixture solution, 45 g of the core particles and 55 g of the functional pigment are used.

BRIEF DESCRIPTION OF THE DRAWINGS

The above and other objects, features and advantages of the present invention will be more clearly understood from the following detailed description taken in conjunction with the accompanying drawing, in which.

DETAILED DESCRIPTION OF THE INVENTION

Figure 1:
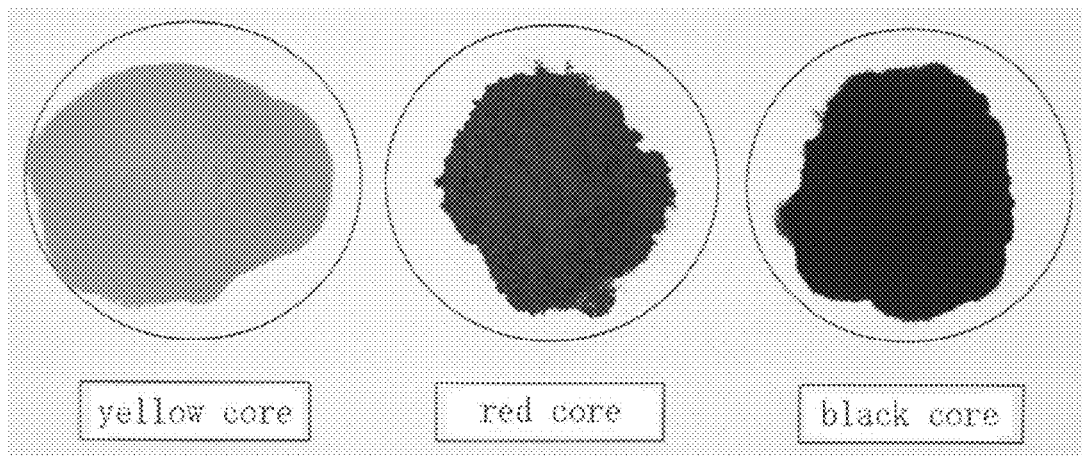
FIG. 1 shows photographs of core particles prepared in Examples 1, 6 and 11.

A color capsule composition for cosmetics according to the present invention is produced by uniformly mixing a color pigment, a plasticizer and a polymer in a first solvent, drying the mixture to produce core particles, uniformly mixing the core particles, a functional pigment and a second solvent, and drying the resulting mixture.

Also, a method for preparing the color capsule composition for cosmetics according to the present invention comprises the steps of: uniformly mixing a polymer, a plasticizer and a color pigment in a first solvent to produce a first mixture solution; spray-drying the first mixture solution to produce core particles in which the color pigment is coated with the polymer; uniformly mixing the prepared core particles, a functional pigment and a second solvent to produce a second mixture solution; and spray drying the second mixture solution to produce capsule particles in which a coating layer of the functional pigment is formed on the outer surface of the polymer.

The polymer serves to coat the color pigment so as to prevent the color pigment from being dispersed, and it is used in an amount of 5-15 wt % based on the weight of the mixture of the polymer, the plasticizer and color pigment. If the polymer is used in an amount of less than 5 wt %, it will not sufficiently cover the color pigment, and if it is used in an amount of more than 15 wt %, the viscosity of the first mixture solution will rapidly increase, thus making it difficult to control the size or sphericity of the core particles. Examples of the polymer that is used in the present invention include polyester, a polyester emulsion, polyaminomethacylate, polyvinylpyrrolidone, hydroxypropylmethylcellulose, shellac, and the like.

The plasticizer serves to swell the polymer and is used in an amount of 5-15 wt % based on the weight of the mixture of the polymer, the plasticizer and the color pigment. If the plasticizer is used in an amount of less than 5 wt %, the polymer will be weakly swollen, and thus the hardness of the particle will undesirably increase, and if it is used in an amount of more than 15 wt %, the polymer will be strongly swollen, and thus the hardness of the particle hardness will excessively decrease such that the particles will be easy to break. Examples of the plasticizer that is used in the present invention include 1,3-butanediol, polyethylene glycol, dipropylene glycol and the like.

The color pigment is used to give the color of cosmetic, and examples thereof include iron oxide pigments, organic pigments, lake dyes, natural pigments, etc. The color pigment is used in an amount of 70-90 wt % based on the weight of the mixture of the polymer, the plasticizer and the color pigment. If the color pigment is used in an amount of less than 70 wt %, the saturation of the final color will decrease, and if it is used in an amount of more than 90 wt %, the contents of the polymer and the plasticizer will relatively decrease, thus making it difficult to control the particle hardness.

The functional pigment serves to increase the covering power and feeling of the capsule particles prepared and to impart gloss to the capsule particles. It is mixed with the core particle at a ratio of 20-60 wt % (functional pigment):80-40 wt % (core particle). If the functional pigment is used in an amount of more than 60 wt %, the expression of the color of the color pigment in the core particle will be decrease, and if it is used in an amount of less than 40 wt %, the covering power and feeling of the capsule particles will decrease. As this functional pigment, titanium dioxide, zinc oxide or the like is used to improve the covering power of the core particles, boron nitride is used to increase the gloss and feeling of the core particles, and talc or mica is used to increase the feeling of the core particles. Such functional pigments may be used alone or in combination.

Meanwhile, to increase the brittleness of the core particle, fatty acid is preferably further added when preparing the first mixture solution. Examples of the fatty acid that is used in the present invention include stearic acid, palmitic acid, oleic acid, linoleic acid, linolenic acid, etc. The fatty acid is used in an amount of 2-5 wt % based on the weight of the mixture of the polymer, the plasticizer, the color pigment and the fatty acid.

In the method of preparing the color capsule composition for cosmetics, the step of preparing the first mixture solution comprises the sub-steps of: uniformly dissolving the polymer and the plasticizer in the first solvent to form a first solution; dissolving the color pigment in the first solvent to form a second solution; and mixing the first solution with the second solution and uniformly dispersing the mixture to form a third solution. It is preferable to separately prepare the solution of the polymer and the plasticizer and the solution of the color pigment, and then to mix these solutions, but the polymer, the plasticizer and the color pigment may also be mixed with each other at one time. Even when the fatty acid is further added when preparing the first mixture solution, the fatty acid may be uniformly dissolved in the first solvent, and then mixed with the first and second solutions to prepare the third solution. Alternatively, the polymer, the plasticizer, the color pigment and the fatty acid may also be mixed with each other at one time.

Also, in the step of producing the core particles, the spray-dried core particles may be sieved to desired sizes. Preferably, if only core particles having an outer diameter of 150 µm or less are screened by sieving and used, the size of the capsule particles can be controlled. The core particles prepared as described above have a porous structure that boosts the effects thereof.

In the method of preparing the color capsule composition for cosmetics according to the present invention, the step of producing the second mixture solution comprises: stirring the functional pigment in the second solvent to produce a fourth solution; dispersing the core powder, produced in step 1, in the second solvent to produce a fifth solution, mixing the fourth solution and the fifth solution, and uniformly dispersing the mixed solution to produce a sixth solution.

Herein, it is preferable to separately prepare the solution of the functional pigment and the solution of the core particles, and then to mix these solutions before use. However, the functional pigment and the core particles may also be mixed with each other at one time and used.

In the step of producing the capsule particles, the spray-dried capsule particles may be sieved to desired sizes. Preferably, if only capsule particles having an outer diameter of 150 µm or less are screened, the covering power of these particles in cosmetic formulations can be enhanced.

In the capsule particles prepared as described above, the functional pigment that forms the coating layer on the core particles can improve the color, covering power and feeling of the capsule particles.

Hereinafter, the present invention will be described in detail with reference to examples.

EXAMPLES 1 TO 30

Example 1

In 43 ml of acetone in an organic solvent, 4.5 g of a polyester polymer and 2.25 g of 1,3-butanediol as a plasticizer were dissolved by stirring at 25° C. for 15 minutes to prepare a solution. Meanwhile, 39.15 g of yellow iron oxide as an inorganic pigment was dispersed in 90 ml of acetone at 25° C. for 15 minutes to prepare a dispersion. The above solution was mixed with and uniformly dispersed in the above dispersion at the same temperature for 30 minutes. Then, the solution was fed into an atomizer (rotating at a high speed of 10,000 rpm) at a constant rate of 100 ml/min using a metering pump. Herein, the solution was fed into the atomizer at 80° C. and dried therein at 60° C. to obtain first cote powder. The obtained core powder was screened through a sieve having a mesh size of 150 μm, thus obtaining core powder having an outer diameter of 150 μm or less.

Meanwhile, 5 g of boron nitride and 50 of titanium dioxide were stirred in 100 ml of distilled water at 25° C. for 10 minutes to obtain an inorganic suspension. Then, 45 g of the obtained core powder was dispersed by stirring in a mixed solution of 207 ml and 23 ml of ethanol at 25° C. for 10 minutes. The above two solutions were mixed with stirring at 25° C. for 10 minutes, and the mixed solution was fed into an atomizer (rotating at a high speed of 10,000 rpm) at a constant rate of 120 ml/min using a metering pump. Herein, the mixed solution was fed into the atomizer at 160° C. and dried therein at 80° C., thus obtaining second capsule powder. The obtained capsule powder was screened through a sieve having a mesh size of 150 μm, thus obtaining second capsule powder having an outer diameter of 150 μm or less.

Example 2

Uniform particles were obtained in the same manner as Example 1, except that the plasticizer was used in an amount of 3.60 parts by weight.

Example 3

Uniform particles were obtained in the same manner as Example 1, except that the plasticizer was used in an amount of 4.50 parts by weight.

Example 4

Uniform particles were obtained in the same manner as Example 1, except that the plasticizer was used in an amount of 6.70 parts by weight.

Example 5

Uniform particles were obtained in the same manner as Example 1, except that the plasticizer was used in an amount of 9.00 parts by weight.

Example 6

Uniform particles were obtained in the same manner as Example 1, except that red iron oxide was used as the inorganic pigment.

Example 7

Uniform particles were obtained in the same manner as Example 6, except that the plasticizer was used in an amount of 3.60 parts by weight.

Example 8

Uniform particles were obtained in the same manner as Example 6, except that the plasticizer was used in an amount of 4.50 parts by weight.

Example 9

Uniform particles were obtained in the same manner as Example 6, except that the plasticizer was used in an amount of 6.70 parts by weight.

Example 9

Uniform particles were obtained in the same manner as Example 6, except that the plasticizer was used in an amount of 9.00 parts by weight.

Example 11

Uniform particles were obtained in the same manner as Example 1, except that black iron oxide was used as the inorganic pigment.

Example 12

Uniform particles were obtained in the same manner as Example 11, except that the plasticizer was used in an amount of 3.60 parts by weight.

Example 13

Uniform particles were obtained in the same manner as Example 11, except that the plasticizer was used in an amount of 4.50 parts by weight.

Example 14

Uniform particles were obtained in the same manner as Example 11, except that the plasticizer was used in an amount of 6.70 parts by weight.

Example 15

Uniform particles were obtained in the same manner as Example 11, except that the plasticizer was used in an amount of 9.00 parts by weight.

Measurement of Brittleness of Particles

The brittleness of each of the capsule powders prepared in Examples 1 to 15 was measured by applying a constant load of 5 gf/cm$^2$ to 0.3 g of the capsule powder while moving the capsule powder in the up, down, left and right directions at a constant speed of 0.01 m/sec for 30 seconds. The capsule powder was observed with an optical microscope, and the number of broken particles per 1 mm×1 mm pixel was measured three times. The measurements were averaged and the results are shown in Table 1 below. In Table 1, the smaller the number of normal particles, the better the brittleness.

TABLE 1

|  | Polymer | Plasticizer | Yellow pigment | Boron nitride | Titanium dioxide | Brittleness of capsule particles (number of normal particles) |
|---|---|---|---|---|---|---|
| Example 1 | 4.5 | 2.25 | 38.25 | 5 | 50 | 14-18 |
| Example 2 | 4.5 | 3.60 | 38.25 | 5 | 50 | 9-14 |
| Example 3 | 4.5 | 4.50 | 38.25 | 5 | 50 | 5-9 |
| Example 4 | 4.5 | 6.75 | 38.25 | 5 | 50 | 2-5 |
| Example 5 | 4.5 | 9.00 | 38.25 | 5 | 50 | 0-2 |

|  | Polymer | Plasticizer | Red pigment | Boron nitride | Titanium dioxide | Brittleness of capsule particles (number of normal particles) |
|---|---|---|---|---|---|---|
| Example 6 | 4.5 | 2.25 | 38.25 | 5 | 50 | 15-20 |
| Example 7 | 4.5 | 3.60 | 38.25 | 5 | 50 | 10-15 |
| Example 8 | 4.5 | 4.50 | 38.25 | 5 | 50 | 6-10 |
| Example 9 | 4.5 | 6.75 | 38.25 | 5 | 50 | 3-6 |
| Example 10 | 4.5 | 9.00 | 38.25 | 5 | 50 | 0-3 |

|  | Polymer | Plasticizer | Black pigment | Boron nitride | Titanium dioxide | Brittleness of capsule particles (number of normal particles) |
|---|---|---|---|---|---|---|
| Example 11 | 4.5 | 2.25 | 38.25 | 5 | 50 | 15-20 |
| Example 12 | 4.5 | 3.60 | 38.25 | 5 | 50 | 10-15 |
| Example 13 | 4.5 | 4.50 | 38.25 | 5 | 50 | 6-10 |
| Example 14 | 4.5 | 6.75 | 38.25 | 5 | 50 | 3-6 |
| Example 14 | 4.5 | 9.00 | 38.25 | 5 | 50 | 0-3 |

As can be seen in Table 1 above, as the amount of the plasticizer decreased, the brittleness of the capsule particles decreased. It can be seen that, if this brittleness is low, when W/O emulsion type cosmetic, W/S emulsion type cosmetic and O/W emulsion type cosmetic products which contain the capsule particles are used, the polymer can be easily applied to the skin. Also, it can be seen that the non-smooth feeling caused by the non-brittle particles on the skin can be reduced.

Measurement of Color Coordinates of Particles

Figure 2:
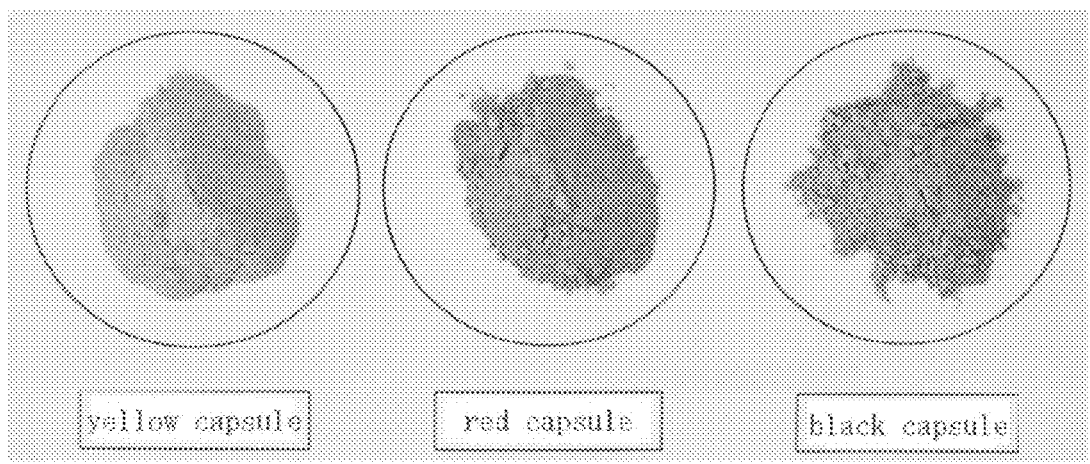
FIG. 2 shows photographs of capsule powders prepared in Examples 1, 6 and 11.

FIG. 1 shows core particles prepared in Examples 1, 6 and 11, and FIG. 2 shows photographs of capsule powders. Also, the covering capacity obtained by the color coordinates of the capsule particles prepared in Examples 1, 6 and 11 is shown in Table 2 below. Herein, the term "covering capacity" refers to the capacity to change one value of coordinates (L, a and b), the term "increase in covering capacity" means that, in the case of the capsule particles containing the yellow pigment, the change Δb* between the color coordinates (L, a and b) of the core and the color coordinates of the capsule is greater than zero, and in the case of the capsule particles containing the red pigment, the change Δa* between the color coordinates (L, a and b) of the core and the color coordinates (L, a and b) of the capsule is greater than zero, and also in the case of the capsule particles containing the black pigment, the change ΔL* between the color coordinates (L, a and b) of the core and the color coordinates (L, a and b) of the capsule is greater than zero. Namely, "ΔL*", "Δa*" and "Δb*" mean $\Delta L^* = [L_{capsule} - L_{core}]$, $\Delta a^* = [a_{core} - a_{capsule}]$, and $\Delta b^* = [b_{core} - b_{capsule}]$, respectively. Meanwhile, "a*" is the saturation for red, and a higher a* value indicates a deeper red. "b*" is the saturation for yellow, and a higher b* value indicates a deeper yellow. In addition, and a higher L* value indicates a lighter color.

TABLE 2

Change in color coordinates according to the kind of particles

| Kind |  |  | Core particles | Capsule particles |
|---|---|---|---|---|
|  |  | pigment particles |  |  |
|  |  | Yellow pigment particles |  |  |
| Color coordinates | L* | 75.512 | 59.477 | 81.608 |
|  | a* | 13.400 | 11.472 | 4.827 |
|  | b* | 49.854 | 41.263 | 11.129 |
|  | Δa* | 30.134 |  |  |
|  |  | Red pigment particles |  |  |
|  | L* | 40.706 | 28.716 | 68.823 |
|  | a* | 30.153 | 19.266 | 10.595 |
|  | b* | 29.945 | 17.906 | 7.626 |
|  | Δa* | 8.671 |  |  |
|  |  | Black pigment particles |  |  |
|  | L* | 16.552 | 14.094 | 65.366 |
|  | a* | -2.077 | -2.435 | -3.014 |
|  | b* | -1.079 | -0.950 | -4.618 |
|  | Δa* | 51.272 |  |  |

As can be seen in FIGS. 1 and 2 and Table 2 above, even when the yellow pigment, the red pigment and the black pigment were used, ΔL* generally increased, and thus the covering power of the capsule particles increased compared to the covering power of the core particles. In the case of the capsule particles containing the red pigment, the saturation Δa* for red generally decreased, and in the case of the capsule particles containing the yellow pigment, the saturation Δb* for yellow generally decreased. This suggests that the covering power of the capsule particles was higher than that of the core particles.

Measurement of Color Expression of Capsule Particles

Examples 16 to 20

Uniform particles were obtained in the same manner as Example 1 using constant amounts of the polymer, the plasticizer and boron nitrogen while changing the amounts of yellow pigment and titanium dioxide added, as shown in Table 3 below. The capsule particles were subjected to color analysis (ΔE*), and the results of the analysis are shown in Table 3 below.

Examples 21 to 25

Uniform particles were obtained in the same manner as Example 1 using constant amounts of the polymer, the plasticizer and boron nitrogen while changing the amounts of red pigment and titanium dioxide added, as shown in Table 3 below. The capsule particles were subjected to color analysis (ΔE*), and the results of the analysis are shown in Table 3 below.

Examples 26 to 30

Uniform particles were obtained in the same manner as Example 1 using constant amounts of the polymer, the plasticizer and boron nitrogen while changing the amounts of yellow pigment and titanium dioxide added, as shown in Table 3 below. The capsule particles were subjected to color analysis (ΔE*), and the results of the analysis are shown in Table 3 below.

TABLE 3

|  | Polymer | Plasticizer | Yellow pigment | Boron nitride | Titanium dioxide | ΔE* |
|---|---|---|---|---|---|---|
| Example 16 | 4.5 | 3.60 | 28 | 5 | 58.9 | 30.32 |
| Example 17 | 4.5 | 3.60 | 39 | 5 | 47.9 | 25.05 |
| Example 18 | 4.5 | 3.60 | 50 | 5 | 36.9 | 19.48 |
| Example 19 | 4.5 | 3.60 | 61 | 5 | 25.9 | 13.51 |
| Example 20 | 4.5 | 3.60 | 72 | 5 | 14.9 | 9.45 |

|  | Polymer | Plasticizer | Red pigment | Boron nitride | Titanium dioxide | ΔE* |
|---|---|---|---|---|---|---|
| Example 21 | 4.5 | 3.60 | 28 | 5 | 58.9 | 48.78 |
| Example 22 | 4.5 | 3.60 | 39 | 5 | 47.9 | 41.23 |
| Example 23 | 4.5 | 3.60 | 50 | 5 | 36.9 | 33.04 |
| Example 24 | 4.5 | 3.60 | 61 | 5 | 25.9 | 20.78 |
| Example 25 | 4.5 | 3.60 | 72 | 5 | 14.9 | 10.35 |

|  | Polymer | Plasticizer | Black pigment | Boron nitride | Titanium dioxide | ΔE* |
|---|---|---|---|---|---|---|
| Example 26 | 4.5 | 3.60 | 28 | 5 | 58.9 | 45.43 |
| Example 27 | 4.5 | 3.60 | 39 | 5 | 47.9 | 38.75 |
| Example 28 | 4.5 | 3.60 | 50 | 5 | 36.9 | 27.42 |
| Example 29 | 4.5 | 3.60 | 61 | 5 | 25.9 | 17.49 |
| Example 30 | 4.5 | 3.60 | 72 | 5 | 14.9 | 7.58 |

1 g of each of the capsule powders prepared in Examples 16 to 30 was applied to a gauze of 5 cm×5 cm by repeatedly moving the capsule powders in the up, down, left and right directions at a constant speed of 0.01 m/sec for 30 seconds while applying a load of 10 gf/cm² so as to be broken. The expressed color of the capsule powders was measured three times using the L*a*b* color system, and the measurements were averaged. Also, the color coordinates of the capsule particles before application were measured. Based on the measured values, the ΔE* value of the capsule particles was calculated, and the results of the calculation are shown in Table 3 above.

Herein, ΔE* means the change between the color coordinates ($L_1$, $a_1$ and $b_1$) of the capsule particles and the color coordinates ($L_2$, $a_2$ and $b_2$) of the broken capsule particles applied to the gauze. Namely, $\Delta E^* = \sqrt{(L_2-L_1)+(a_2-a_1)+(b_2-b_1)}$.

As can be seen in Table 3 above, the yellow capsules containing the yellow pigment had a color value of 9.45≤ΔE≥30.52, the red capsules containing the red pigment had a color value of 10.35≤ΔE≥48.78, and the black capsules containing the black pigment had a color value of 7.58≤ΔE≥45.43.

Examples 31 to 225

Preparation of Core Powders Having Color

Example 31

Preparation of Core Powder Consisting of Polymer-Plasticizer-Iron Oxide Pigment

The preparation of core particles, which is the first step of the process for preparing the core particles having a color, was performed in the following manner.

Inner cores containing an iron oxide pigment (yellow iron oxide, black iron oxide, red iron oxide, or a mixture of two or more thereof) were prepared in the following manner. In 43 ml of acetone, 3.6 g of a polyester polymer and 2.25 g of 1,3-butanediol were dissolved by stirring at 25° C. for 15 minutes to prepare a solution. Meanwhile, 39.15 g of an iron oxide pigment was dispersed in 90 ml of acetone at 25° C. for 15 minutes to prepare a dispersion. The above solution was mixed with and uniformly dispersed in the above dispersion for 30 minutes at the same temperature.

Then, the resulting solution was fed into an atomizer (rotating at a high speed of 10,000 rpm) at a rate of 100 ml/min using a metering pump. Herein, the solution was fed into the atomizer at 80° C. and dried therein at 60° C. to obtain core powder. Herein, the obtained core powder had an outer diameter ranging from 10 μm to 150 μm.

Examples 32 to 57

Preparation of Core Powders Using Varying Kinds and Contents of Plasticizer

Figure 3:
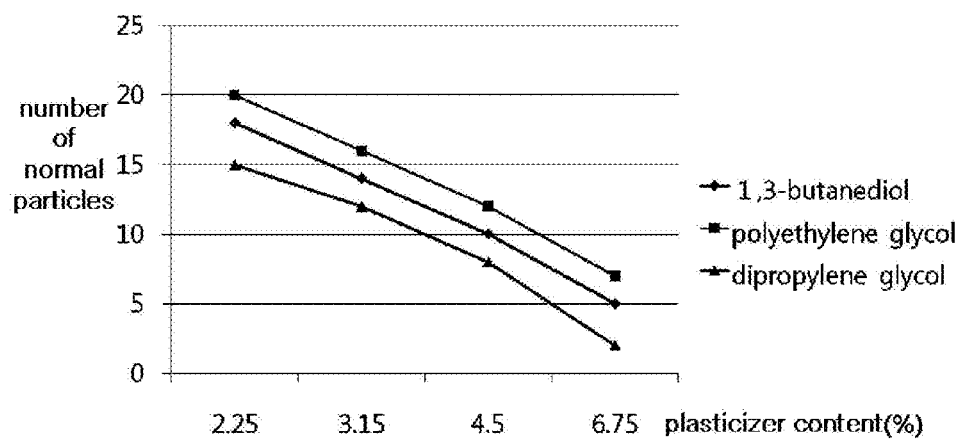
FIGS. 3 and 4 are graphic diagrams showing the brittleness of core powders of Examples 31 to 57.
Figure 4:
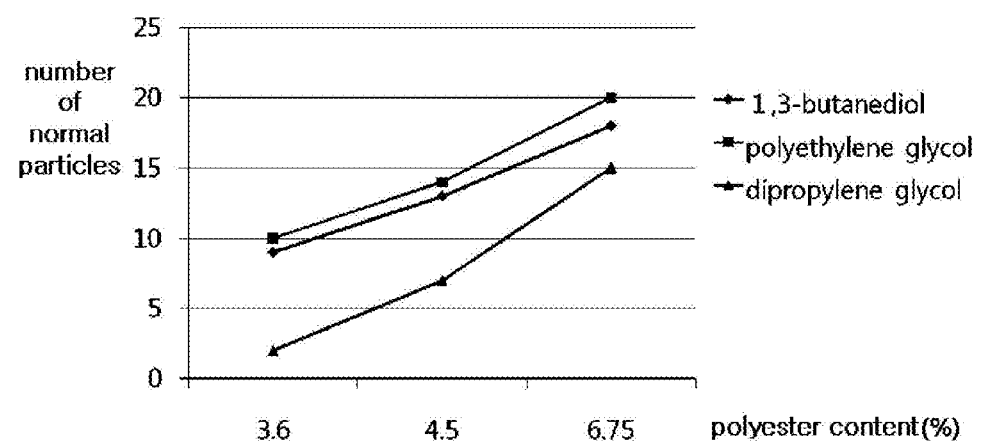

Core powders were prepared in the same manner as Example 31. The specific kinds and contents of compounds used herein are shown in Table 4 below. The brittleness of the core powders according to changes in the amount of the plasticizer and the amount of the polyester polymer was measured, and the results of the measurement are shown in FIGS. 3 and 4.

TABLE 4

|  | Step 1 | | | | | |
|---|---|---|---|---|---|---|
|  | Polymer | | Plasticizer | | Pigment | |
| Example 31 | Polyester | 3.60 | 1,3-butanediol | 2.25 | Iron oxide pigment | 39.15 |
| Example 32 | Polyester | 3.60 | 1,3-butanediol | 3.15 | Iron oxide pigment | 38.25 |
| Example 33 | Polyester | 4.50 | 1,3-butanediol | 2.25 | Iron oxide pigment | 38.25 |

TABLE 4-continued

| | Step 1 | | | | | |
|---|---|---|---|---|---|---|
| | Polymer | | Plasticizer | | Pigment | |
| Example 34 | Polyester | 4.50 | 1,3-butanediol | 3.15 | Iron oxide pigment | 37.35 |
| Example 35 | Polyester | 4.50 | 1,3-butanediol | 4.50 | Iron oxide pigment | 36.00 |
| Example 36 | Polyester | 6.75 | 1,3-butanediol | 2.25 | Iron oxide pigment | 36.00 |
| Example 37 | Polyester | 6.75 | 1,3-butanediol | 3.15 | Iron oxide pigment | 35.10 |
| Example 38 | Polyester | 6.75 | 1,3-butanediol | 4.50 | Iron oxide pigment | 33.75 |
| Example 39 | Polyester | 6.75 | 1,3-butanediol | 6.75 | Iron oxide pigment | 31.50 |
| Example 40 | Polyester | 3.60 | Polyethylene glycol | 2.25 | Iron oxide pigment | 39.15 |
| Example 41 | Polyester | 3.60 | Polyethylene glycol | 3.15 | Iron oxide pigment | 38.25 |
| Example 42 | Polyester | 4.50 | Polyethylene glycol | 2.25 | Iron oxide pigment | 38.25 |
| Example 43 | Polyester | 4.50 | Polyethylene glycol | 3.15 | Iron oxide pigment | 37.35 |
| Example 44 | Polyester | 4.50 | Polyethylene glycol | 4.30 | Iron oxide pigment | 36.00 |
| Example 45 | Polyester | 6.75 | Polyethylene glycol | 2.25 | Iron oxide pigment | 36.00 |
| Example 46 | Polyester | 6.75 | Polyethylene glycol | 3.15 | Iron oxide pigment | 35.10 |
| Example 47 | Polyester | 6.75 | Polyethylene glycol | 4.50 | Iron oxide pigment | 33.75 |
| Example 48 | Polyester | 6.75 | Polyethylene glycol | 6.75 | Iron oxide pigment | 31.50 |
| Example 49 | Polyester | 3.60 | Dipropylene glycol | 2.25 | Iron oxide pigment | 39.15 |
| Example 50 | Polyester | 3.60 | Dipropylene glycol | 3.15 | Iron oxide pigment | 38.35 |
| Example 51 | Polyester | 4.50 | Dipropylene glycol | 2.25 | Iron oxide pigment | 38.25 |
| Example 52 | Polyester | 4.50 | Dipropylene glycol | 3.15 | Iron oxide pigment | 37.35 |
| Example 53 | Polyester | 4.50 | Dipropylene glycol | 4.50 | Iron oxide pigment | 36.00 |
| Example 54 | Polyester | 6.75 | Dipropylene glycol | 2.25 | Iron oxide pigment | 36.00 |
| Example 55 | Polyester | 6.75 | Dipropylene glycol | 3.15 | Iron oxide pigment | 35.10 |
| Example 56 | Polyester | 6.75 | Dipropylene glycol | 4.50 | Iron oxide pigment | 33.75 |
| Example 57 | Polyester | 6.75 | Dipropylene glycol | 6.75 | Iron oxide pigment | 31.50 |

As can be seen from the graphs of FIGS. 3 and 4, with respect to brittleness according to the kind of plasticizer, 1,3-butanediol or dipropylene glycol having a relatively low molecular weight showed improved brittleness compared to polyethylene glycol having a relatively high molecular weight. Also, dipropylene glycol or polyethylene glycol having a high volatilization temperature had a relatively excellent brittleness. Also, it can be seen that, as the amount of the plasticizer increased, the brittleness of the capsule particles increased (the number of normal particles decreased), and as the amount of the polymer increased, the brittleness of the capsule particles decreased (the number of normal particles increased). It can be seen that the dipropylene glycol plasticizer satisfying such two conditions is preferable. In addition, it can be seen that, as the amount of the plasticizer increased, the brittleness of the core powders increased (the number of normal particles decreased), and as the amount of the polymer increased, the brittleness of the core particles decreased (the number of normal particles increased).

Examples 58 to 63

Preparation of Core Powders Using Varying Amounts of Polyester Polymer and Plasticizer with Addition of Fatty Acid Core powders were prepared in same manner as Example 31, except that a mixture of polyethylene glycol and dipropylene glycol was used as the plasticizer and that stearic acid as fatty acid was also added during the dissolution process. The specific kinds and contents of compounds used herein are shown in Table 5 below. The brittleness of core powders according to changes in the amount of fatty acid was measured, and the results of the measurement are shown in FIG. 5.

TABLE 5

| | Sep 1 | | | | | | | | | |
|---|---|---|---|---|---|---|---|---|---|---|
| | Polymer | | Plasticizer | | | | Fatty acid | | Pigment | |
| Example 58 | Polyester | 4.50 | Polyethylene glycol | 1.00 | Dipropylene glycol | 2.15 | Stearic acid | 2.00 | Iron oxide pigment | 35.35 |
| Example 59 | Polyester | 4.50 | Polyethylene glycol | 2.00 | Dipropylene glycol | 2.50 | Stearic acid | 2.00 | Iron oxide pigment | 34.00 |
| Example 60 | Polyester | 4.50 | Polyethylene glycol | 1.00 | Dipropylene glycol | 2.15 | Stearic acid | 1.50 | Iron oxide pigment | 35.85 |
| Example 61 | Polyester | 4.50 | Polyethylene glycol | 2.00 | Dipropylene glycol | 2.50 | Stearic acid | 1.50 | Iron oxide pigment | 34.50 |
| Example 62 | Polyester | 4.50 | Polyethylene glycol | 1.00 | Dipropylene glycol | 2.15 | Stearic acid | 1.00 | Iron oxide pigment | 36.35 |
| Example 63 | Polyester | 4.50 | Polyethylene glycol | 2.00 | Dipropylene glycol | 2.50 | Stearic acid | 1.00 | Iron oxide pigment | 35.00 |

Figure 5:
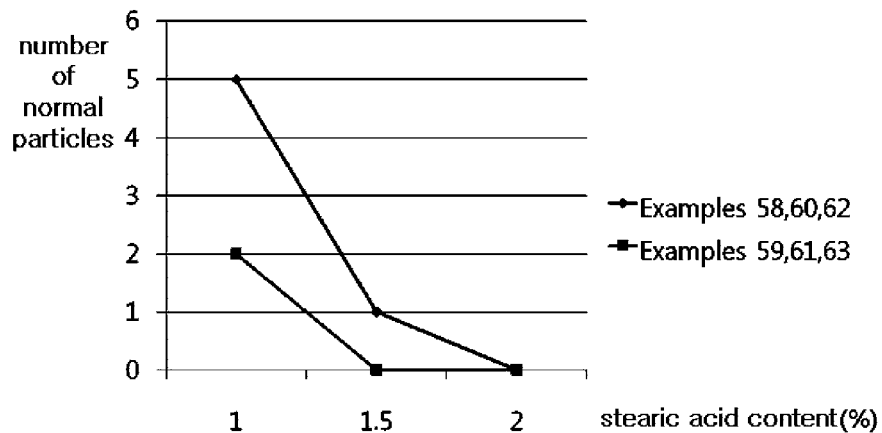
FIG. 5 is a graphic diagram showing the brittleness of core powders of Examples 58 to 63 according to a change in the amount of fatty acid.

As can be seen from the graph of FIG. 5, when the fatty acid was added as the plasticizer, the brittleness of the core particles rapidly increased (the number of normal particles decreased).

Examples 64 to 90

Preparation of Core Powders Using Varying Kinds and Contents of Polyacrylate Polymer and Plasticizer Core powders were prepared in the same manner as Example 31, except that ethanol was used in place of the acetone solvent, used in step 1 of the preparation process of Example 31, to disperse or dissolve the polymer and the iron oxide pigment. The specific kinds and contents of compounds used herein are shown in Table 6 below. The brittleness of the core particles according to changes in the amounts of plasticizer and polyaminomethacrylate polymer used was measured, and the results of the measurement are shown in FIGS. 6 and 7.

TABLE 6

|  | Step 1 | | | | | |
|---|---|---|---|---|---|---|
|  | Polymer | | Plasticizer | | Pigment | |
| Example 64 | Polyaminomethacrylate | 3.60 | 1,3-butanediol | 2.25 | Iron oxide pigment | 39.15 |
| Example 65 | Polyaminomethacrylate | 3.60 | 1,3-butanediol | 3.15 | Iron oxide pigment | 38.25 |
| Example 66 | Polyaminomethacrylate | 4.50 | 1,3-butanediol | 2.25 | Iron oxide pigment | 38.25 |
| Example 67 | Polyaminomethacrylate | 4.50 | 1,3-butanediol | 3.15 | Iron oxide pigment | 37.35 |
| Example 68 | Polyaminomethacrylate | 4.50 | 1,3-butanediol | 4.50 | Iron oxide pigment | 36.00 |
| Example 69 | Polyaminomethacrylate | 6.75 | 1,3-butanediol | 2.25 | Iron oxide pigment | 36.00 |
| Example 70 | Polyaminomethacrylate | 6.75 | 1,3-butanediol | 3.15 | Iron oxide pigment | 35.10 |
| Example 71 | Polyaminomethacrylate | 6.75 | 1,3-butanediol | 4.50 | Iron oxide pigment | 33.75 |
| Example 72 | Polyaminomethacrylate | 6.75 | 1,3-butanediol | 6.75 | Iron oxide pigment | 31.50 |
| Example 73 | Polyaminomethacrylate | 3.60 | Polyethylene glycol | 2.25 | Iron oxide pigment | 39.15 |
| Example 74 | Polyaminomethacrylate | 3.60 | Polyethylene glycol | 3.15 | Iron oxide pigment | 38.25 |
| Example 75 | Polyaminomethacrylate | 4.50 | Polyethylene glycol | 2.25 | Iron oxide pigment | 38.25 |
| Example 76 | Polyaminomethacrylate | 4.50 | Polyethylene glycol | 3.15 | Iron oxide pigment | 37.35 |
| Example 77 | Polyaminomethacrylate | 4.50 | Polyethylene glycol | 4.50 | Iron oxide pigment | 36.00 |
| Example 78 | Polyaminomethacrylate | 6.75 | Polyethylene glycol | 2.25 | Iron oxide pigment | 36.00 |
| Example 79 | Polyaminomethacrylate | 6.75 | Polyethylene glycol | 3.15 | Iron oxide pigment | 35.10 |
| Example 80 | Polyaminomethacrylate | 6.75 | Polyethylene glycol | 4.50 | Iron oxide pigment | 33.75 |
| Example 81 | Polyaminomethacrylate | 6.75 | Polyethylene glycol | 6.75 | Iron oxide pigment | 31.50 |
| Example 82 | Polyaminomethacrylate | 3.60 | Dipropylene glycol | 2.25 | Iron oxide pigment | 39.15 |
| Example 83 | Polyaminomethacrylate | 3.60 | Dipropylene glycol | 3.15 | Iron oxide pigment | 38.25 |
| Example 84 | Polyaminomethacrylate | 4.50 | Dipropylene glycol | 2.25 | Iron oxide pigment | 38.25 |
| Example 85 | Polyaminomethacrylate | 4.50 | Dipropylene glycol | 3.15 | Iron oxide pigment | 37.35 |
| Example 86 | Polyaminomethacrylate | 4.50 | Dipropylene glycol | 4.50 | Iron oxide pigment | 36.00 |
| Example 87 | Polyaminomethacrylate | 6.75 | Dipropylene glycol | 2.25 | Iron oxide pigment | 36.00 |
| Example 88 | Polyaminomethacrylate | 6.75 | Dipropylene glycol | 3.15 | Iron oxide pigment | 35.10 |
| Example 89 | Polyaminomethacrylate | 6.75 | Dipropylene glycol | 4.50 | Iron oxide pigment | 33.75 |
| Example 90 | Polyaminomethacrylate | 6.75 | Dipropylene glycol | 6.75 | Iron oxide pigment | 31.50 |

Figure 6:
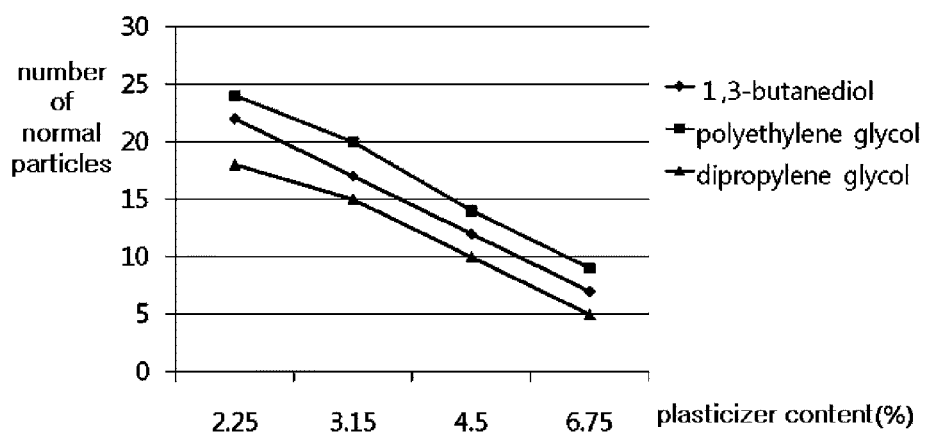
FIGS. 6 and 7 are graphic diagrams showing the brittleness of core powders of Examples 64 to 90.
Figure 7:
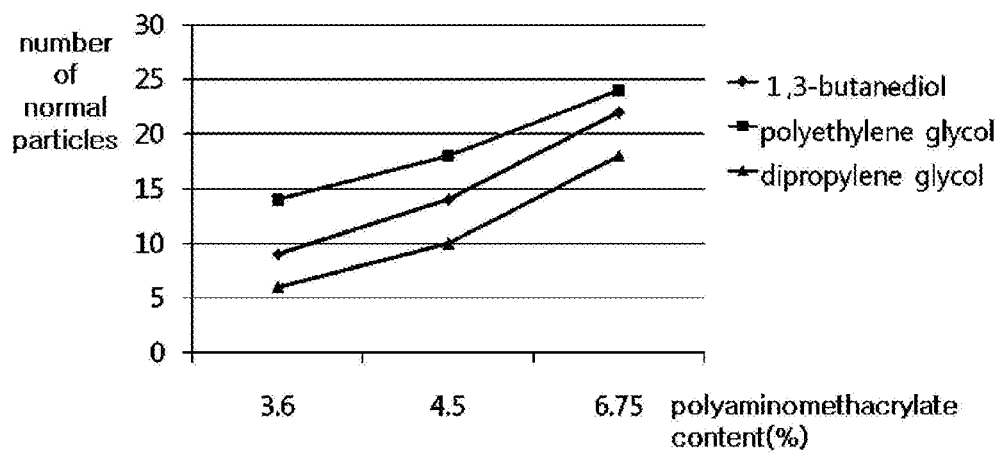

As can be seen from the graphs of FIGS. 6 and 7, like the case of Examples 31 to 57, the use of dipropylene glycol as the plasticizer showed the most excellent brittleness (the number of normal particles decreased), even when polyaminomethacrylate was used as the polymer. Also, it can be seen that, as the amount of the polymer increased, the brittleness of the capsule particles decreased (the number of normal particles increased).

Examples 91 to 171

Figure 8:
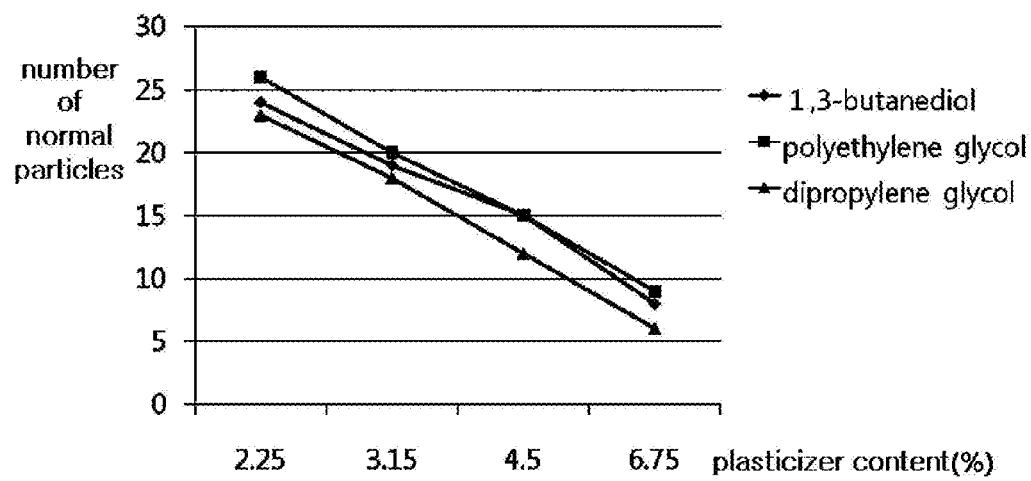
FIGS. 8 and 9 are graphic diagrams showing the brittleness of core powders of Examples 91 to 117.
Figure 9:
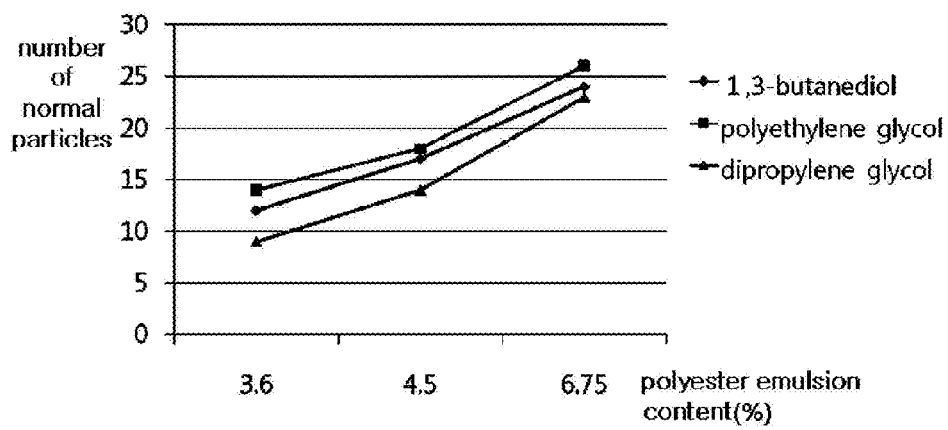
Figure 10:
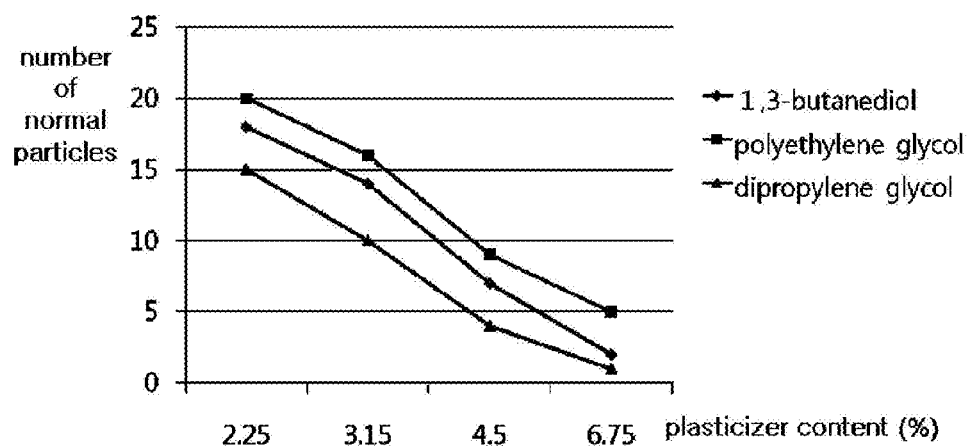
FIGS. 10 and 11 are graphic diagrams showing the brittleness of core powders of Examples 118 to 144.
Figure 11:
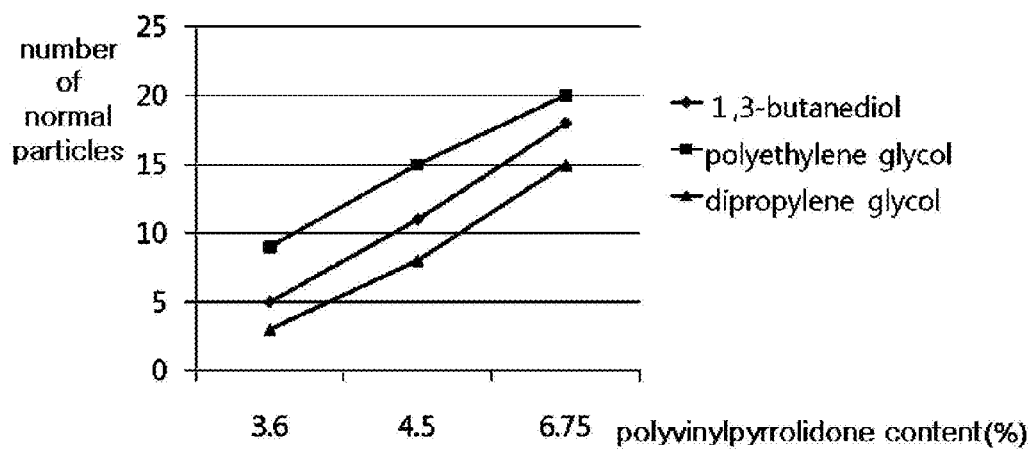
Figure 12:
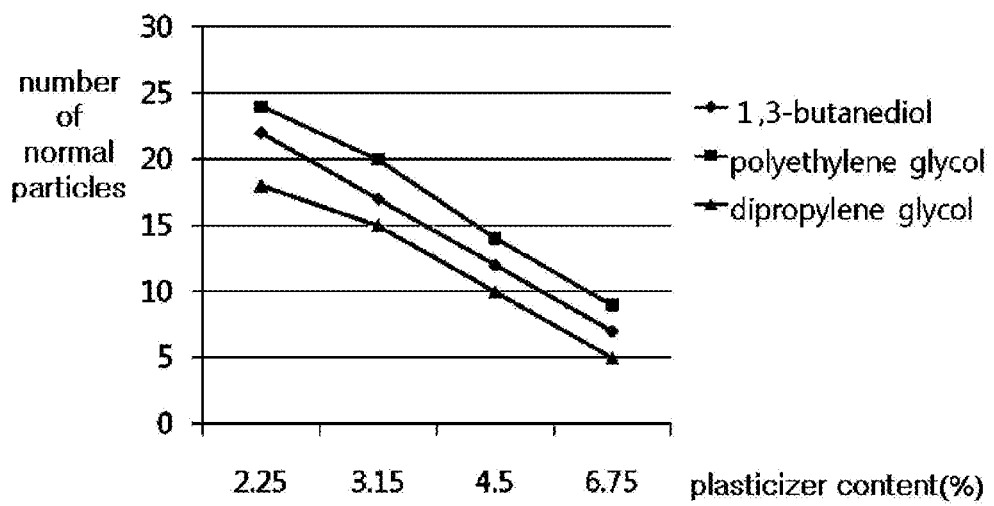
FIGS. 12 and 13 are graphic diagrams showing the brittleness of core powders of Examples 145 to 171.
Figure 13:
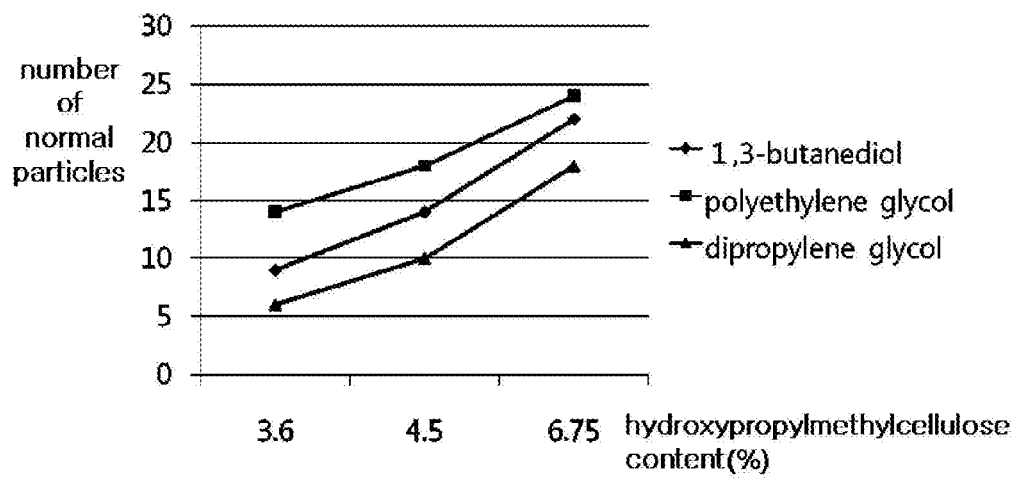

Preparation of Core Powders from Water-Dispersible or Water-Soluble Polymer Using Varying Kinds and Contents of Plasticizer Core powders were prepared in the same manner as Example 31, except that distilled water was used in place of the acetone solvent, used in step 1 of the preparation process of Example 31, to disperse or dissolve the polymer and the iron oxide pigment. The specific kinds and contents of compounds used herein are shown in Table 7 below. The brittleness of the core powders of Examples 91 to 117 according to changes in the amounts of plasticizer and polyester polymer used was measured, and the results of the measurement are shown in FIGS. 8 and 9. Also, the brittleness of the core powders of Examples 118 to 144 according to changes in the amounts of plasticizer and polyvinylpyrrolidone used was measured, and the results of the measurement are shown in FIGS. 10 and 11. In addition, the brittleness of the core powders of Examples 145 to 171 according to changes in the amounts of plasticizer and hydroxypropylmethylcellulose used was measured, and the results of the measurement are shown in FIGS. 12 and 13.

TABLE 7

| | | | Step 1 | | | |
|---|---|---|---|---|---|---|
| | Polymer | | Plasticizer | | Pigment | |
| Example 91 | Polyester emulsion | 3.60 | 1,3-butanediol | 2.25 | Iron oxide pigment | 39.15 |
| Example 92 | Polyester emulsion | 3.60 | 1,3-butanediol | 3.15 | Iron oxide pigment | 38.25 |
| Example 93 | Polyester emulsion | 4.50 | 1,3-butanediol | 2.25 | Iron oxide pigment | 38.25 |
| Example 94 | Polyester emulsion | 4.50 | 1,3-butanediol | 3.15 | Iron oxide pigment | 37.35 |
| Example 95 | Polyester emulsion | 4.50 | 1,3-butanediol | 4.50 | Iron oxide pigment | 36.00 |
| Example 96 | Polyester emulsion | 6.75 | 1,3-butanediol | 2.25 | Iron oxide pigment | 36.00 |
| Example 97 | Polyester emulsion | 6.75 | 1,3-butanediol | 3.15 | Iron oxide pigment | 35.10 |
| Example 98 | Polyester emulsion | 6.75 | 1,3-butanediol | 4.50 | Iron oxide pigment | 33.75 |
| Example 99 | Polyester emulsion | 6.75 | 1,3-butanediol | 6.75 | Iron oxide pigment | 31.50 |
| Example 100 | Polyester emulsion | 3.60 | Polyethylene glycol | 2.25 | Iron oxide pigment | 39.15 |
| Example 101 | Polyester emulsion | 3.60 | Polyethylene glycol | 3.15 | Iron oxide pigment | 38.25 |
| Example 102 | Polyester emulsion | 4.50 | Polyethylene glycol | 2.25 | Iron oxide pigment | 38.25 |
| Example 103 | Polyester emulsion | 4.50 | Polyethylene glycol | 3.15 | Iron oxide pigment | 37.35 |
| Example 104 | Polyester emulsion | 4.50 | Polyethylene glycol | 4.50 | Iron oxide pigment | 36.00 |
| Example 105 | Polyester emulsion | 6.75 | Polyethylene glycol | 2.25 | Iron oxide pigment | 36.00 |
| Example 106 | Polyester emulsion | 6.75 | Polyethylene glycol | 3.15 | Iron oxide pigment | 35.10 |
| Example 107 | Polyester emulsion | 6.75 | Polyethylene glycol | 4.50 | Iron oxide pigment | 33.75 |
| Example 108 | Polyester emulsion | 6.75 | Polyethylene glycol | 6.75 | Iron oxide pigment | 31.50 |
| Example 109 | Polyester emulsion | 3.60 | Dipropylene glycol | 2.25 | Iron oxide pigment | 39.15 |
| Example 110 | Polyester emulsion | 3.60 | Dipropylene glycol | 3.15 | Iron oxide pigment | 38.25 |
| Example 111 | Polyester emulsion | 4.50 | Dipropylene glycol | 2.25 | Iron oxide pigment | 38.25 |
| Example 112 | Polyester emulsion | 4.50 | Dipropylene glycol | 3.15 | Iron oxide pigment | 37.35 |
| Example 113 | Polyester emulsion | 4.50 | Dipropylene glycol | 4.50 | Iron oxide pigment | 36.00 |
| Example 114 | Polyester emulsion | 6.75 | Dipropylene glycol | 2.25 | Iron oxide pigment | 36.00 |
| Example 115 | Polyester emulsion | 6.75 | Dipropylene glycol | 3.15 | Iron oxide pigment | 35.10 |
| Example 116 | Polyester emulsion | 6.75 | Dipropylene glycol | 4.50 | Iron oxide pigment | 33.75 |
| Example 117 | Polyester emulsion | 6.75 | Dipropylene glycol | 6.75 | Iron oxide pigment | 31.50 |
| Example 118 | Polyvinylpyrrolidone | 3.60 | 1,3-butanediol | 2.25 | Iron oxide pigment | 39.15 |
| Example 119 | Polyvinylpyrrolidone | 3.60 | 1,3-butanediol | 3.15 | Iron oxide pigment | 38.25 |
| Example 120 | Polyvinylpyrrolidone | 4.50 | 1,3-butanediol | 2.25 | Iron oxide pigment | 38.25 |
| Example 121 | Polyvinylpyrrolidone | 4.50 | 1,3-butanediol | 3.15 | Iron oxide pigment | 37.35 |
| Example 122 | Polyvinylpyrrolidone | 4.50 | 1,3-butanediol | 4.50 | Iron oxide pigment | 36.00 |
| Example 123 | Polyvinylpyrrolidone | 6.75 | 1,3-butanediol | 2.25 | Iron oxide pigment | 36.00 |
| Example 124 | Polyvinylpyrrolidone | 6.75 | 1,3-butanediol | 3.15 | Iron oxide pigment | 35.10 |
| Example 125 | Polyvinylpyrrolidone | 6.75 | 1,3-butanediol | 4.50 | Iron oxide pigment | 33.75 |
| Example 126 | Polyvinylpyrrolidone | 6.75 | 1,3-butanediol | 6.75 | Iron oxide pigment | 31.50 |
| Example 127 | Polyvinylpyrrolidone | 3.60 | Polyethylene glycol | 2.25 | Iron oxide pigment | 39.15 |
| Example 128 | Polyvinylpyrrolidone | 3.60 | Polyethylene glycol | 3.15 | Iron oxide pigment | 38.25 |
| Example 129 | Polyvinylpyrrolidone | 4.50 | Polyethylene glycol | 2.25 | Iron oxide pigment | 38.25 |
| Example 130 | Polyvinylpyrrolidone | 4.50 | Polyethylene glycol | 3.15 | Iron oxide pigment | 37.35 |
| Example 131 | Polyvinylpyrrolidone | 4.50 | Polyethylene glycol | 4.50 | Iron oxide pigment | 36.00 |
| Example 132 | Polyvinylpyrrolidone | 6.75 | Polyethylene glycol | 2.25 | Iron oxide pigment | 36.00 |
| Example 133 | Polyvinylpyrrolidone | 6.75 | Polyethylene glycol | 3.15 | Iron oxide pigment | 35.10 |
| Example 134 | Polyvinylpyrrolidone | 6.75 | Polyethylene glycol | 4.50 | Iron oxide pigment | 33.75 |
| Example 135 | Polyvinylpyrrolidone | 6.75 | Polyethylene glycol | 6.75 | Iron oxide pigment | 31.50 |
| Example 136 | Polyvinylpyrrolidone | 3.60 | Dipropylene glycol | 2.25 | Iron oxide pigment | 39.15 |
| Example 137 | Polyvinylpyrrolidone | 3.60 | Dipropylene glycol | 3.15 | Iron oxide pigment | 38.25 |
| Example 138 | Polyvinylpyrrolidone | 4.50 | Dipropylene glycol | 2.25 | Iron oxide pigment | 38.25 |
| Example 139 | Polyvinylpyrrolidone | 4.50 | Dipropylene glycol | 3.15 | Iron oxide pigment | 37.35 |
| Example 140 | Polyvinylpyrrolidone | 4.50 | Dipropylene glycol | 4.50 | Iron oxide pigment | 36.00 |
| Example 141 | Polyvinylpyrrolidone | 6.75 | Dipropylene glycol | 2.25 | Iron oxide pigment | 36.00 |
| Example 142 | Polyvinylpyrrolidone | 6.75 | Dipropylene glycol | 3.15 | Iron oxide pigment | 35.10 |
| Example 143 | Polyvinylpyrrolidone | 6.75 | Dipropylene glycol | 4.50 | Iron oxide pigment | 33.75 |
| Example 144 | Polyvinylpyrrolidone | 6.75 | Dipropylene glycol | 6.75 | Iron oxide pigment | 31.50 |
| Example 145 | Hydroxypropylmethyl cellulose | 3.60 | 1,3-butanediol | 2.25 | Iron oxide pigment | 39.15 |
| Example 146 | Hydroxypropylmethyl cellulose | 3.60 | 1,3-butanediol | 3.15 | Iron oxide pigment | 38.25 |
| Example 147 | Hydroxypropylmethyl cellulose | 4.50 | 1,3-butanediol | 2.25 | Iron oxide pigment | 38.25 |
| Example 148 | Hydroxypropylmethyl cellulose | 4.50 | 1,3-butanediol | 3.15 | Iron oxide pigment | 37.35 |
| Example 149 | Hydroxypropylmethyl cellulose | 4.50 | 1,3-butanediol | 4.50 | Iron oxide pigment | 36.00 |
| Example 150 | Hydroxypropylmethyl cellulose | 6.75 | 1,3-butanediol | 2.25 | Iron oxide pigment | 36.00 |
| Example 151 | Hydroxypropylmethyl cellulose | 6.75 | 1,3-butanediol | 3.15 | Iron oxide pigment | 35.10 |
| Example 152 | Hydroxypropylmethyl cellulose | 6.75 | 1,3-butanediol | 4.50 | Iron oxide pigment | 33.75 |
| Example 153 | Hydroxypropylmethyl cellulose | 6.75 | 1,3-butanediol | 6.75 | Iron oxide pigment | 31.50 |
| Example 154 | Hydroxypropylmethyl cellulose | 3.60 | Polyethylene glycol | 2.25 | Iron oxide pigment | 39.15 |
| Example 155 | Hydroxypropylmethyl cellulose | 3.60 | Polyethylene glycol | 3.15 | Iron oxide pigment | 38.25 |
| Example 156 | Hydroxypropylmethyl cellulose | 4.50 | Polyethylene glycol | 2.25 | Iron oxide pigment | 38.25 |
| Example 157 | Hydroxypropylmethyl cellulose | 4.50 | Polyethylene glycol | 3.15 | Iron oxide pigment | 37.35 |
| Example 158 | Hydroxypropylmethyl cellulose | 4.50 | Polyethylene glycol | 4.50 | Iron oxide pigment | 36.00 |
| Example 159 | Hydroxypropylmethyl cellulose | 6.75 | Polyethylene glycol | 2.25 | Iron oxide pigment | 36.00 |
| Example 160 | Hydroxypropylmethyl cellulose | 6.75 | Polyethylene glycol | 3.15 | Iron oxide pigment | 35.10 |
| Example 161 | Hydroxypropylmethyl cellulose | 6.75 | Polyethylene glycol | 4.50 | Iron oxide pigment | 33.75 |
| Example 162 | Hydroxypropylmethyl cellulose | 6.75 | Polyethylene glycol | 6.75 | Iron oxide pigment | 31.50 |
| Example 163 | Hydroxypropylmethyl cellulose | 3.60 | Dipropylene glycol | 2.25 | Iron oxide pigment | 39.15 |
| Example 164 | Hydroxypropylmethyl cellulose | 3.60 | Dipropylene glycol | 3.15 | Iron oxide pigment | 38.25 |
| Example 165 | Hydroxypropylmethyl cellulose | 4.50 | Dipropylene glycol | 2.25 | Iron oxide pigment | 38.25 |
| Example 166 | Hydroxypropylmethyl cellulose | 4.50 | Dipropylene glycol | 3.15 | Iron oxide pigment | 37.35 |

TABLE 7-continued

| | Step 1 | | | | | |
|---|---|---|---|---|---|---|
| | Polymer | | Plasticizer | | Pigment | |
| Example 167 | Hydroxypropylmethyl cellulose | 4.50 | Dipropylene glycol | 4.50 | Iron oxide pigment | 36.00 |
| Example 168 | Hydroxypropylmethyl cellulose | 6.75 | Dipropylene glycol | 2.25 | Iron oxide pigment | 36.00 |
| Example 169 | Hydroxypropylmethyl cellulose | 6.75 | Dipropylene glycol | 3,15 | Iron oxide pigment | 35.10 |
| Example 170 | Hydroxypropylmethyl cellulose | 6.75 | Dipropylene glycol | 4.50 | Iron oxide pigment | 33.75 |
| Example 171 | Hydroxypropylmethyl cellulose | 6.75 | Dipropylene glycol | 6.75 | Iron oxide pigment | 31.50 |

As can be seen from the graphs of FIGS. 8 to 13, even when the water-dispersible or water-soluble polymer was used and distilled solvent was used as the solvent, the brittleness of the capsule particles increased (the number of normal particles decreased). This suggests that the capsule particles can be prepared using an environmentally friendly process. Accordingly, it can be seen that the costs of supplementary facilities such as a solvent recovery apparatus and process costs can be reduced, and thus environmentally friendly products can be prepared.

Examples 172 to 198

Preparation of Core Powders from Natural Polymer Using Kinds and Contents of Plasticizer Capsule particles were prepared in the same manner as Example 31, except that shellac was used as the polymer in step 1 of the preparation process of Example 31 and that ethanol was used in place of the acetone solvent to disperse or dissolve the iron oxide pigment. The specific kinds and contents of compounds used herein are shown in Table 8 below. The brittleness of the core powders according to changes in the amounts of plasticizer and shellac polymer used was measured, and the results of the measurement are shown in FIGS. 14 and 15.

Figure 14:
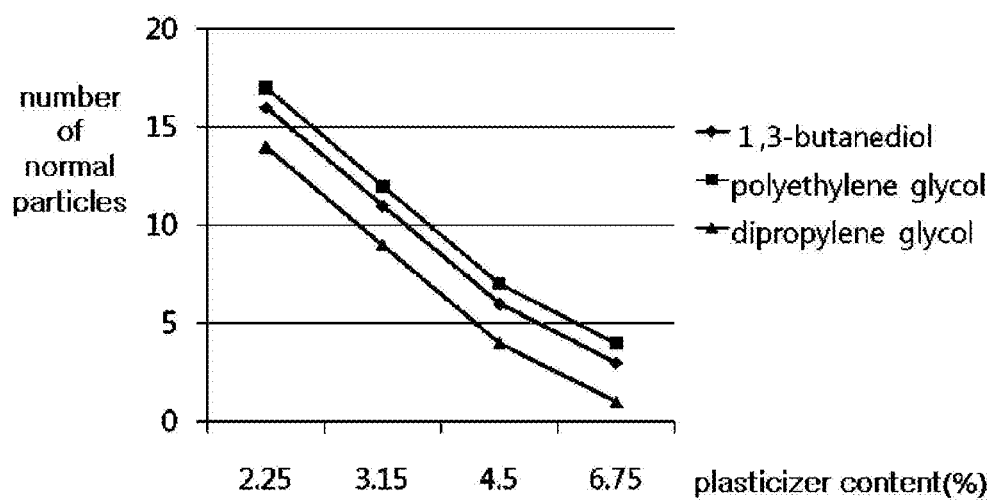
FIGS. 14 and 15 are graphic diagrams showing the brittleness of core powders of Examples 172 to 198.
Figure 15:
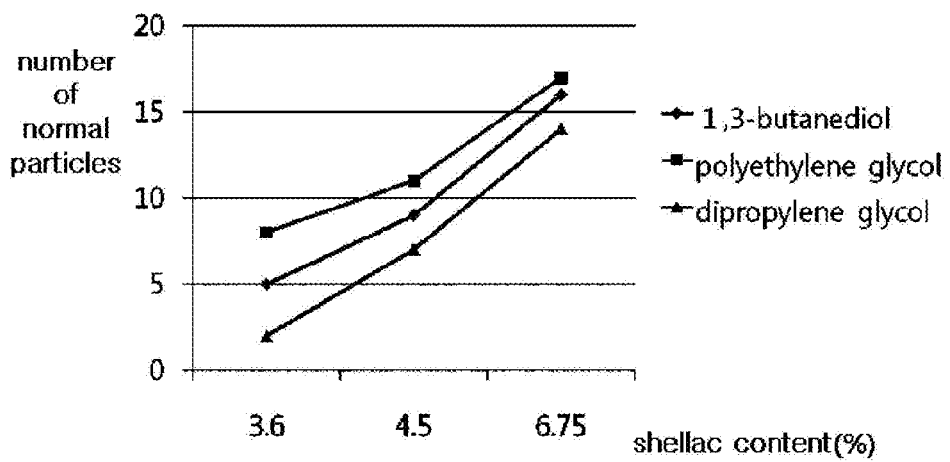

As can be seen from the graphs of FIGS. 14 and 15, even when the core powders prepared using the natural polymer, the brittleness of the capsule particles increased (the number of normal particles decreased). This suggests that environmentally friendly products and Ecocert products can be prepared.

Examples 199 to 207

Preparation of Core Powders Consisting of Polyester Polymer-Plasticizer-Organic Pigment Core powders were prepared in the same manner as Example 31, except that the acetone solvent used in step 1 of the preparation process of Example 31 was used to dissolve dipropylene glycol, a polyester polymer and an organic pigment and that an azo-, indigo- or phthalocyanine-based pigment compound was used as the organic pigment. The kinds and contents of compounds used herein are shown in Tables 9 below.

TABLE 8

| | Step 1 | | | | | |
|---|---|---|---|---|---|---|
| | Polymer | | Plasticizer | | Pigment | |
| Example 171 | Shellac | 3.60 | 1,3-butanedio | 2.25 | Iron oxide pigment | 39.15 |
| Example 173 | Shellac | 3.60 | 1,3-butanedio | 3.15 | Iron oxide pigment | 38.25 |
| Example 174 | Shellac | 4.50 | 1,3-butanedio | 2.25 | Iron oxide pigment | 38/25 |
| Example 175 | Shellac | 4.50 | 1,3-butanedio | 3.15 | Iron oxide pigment | 37.35 |
| Example 176 | Shellac | 4.50 | 1,3-butanedio | 4.50 | Iron oxide pigment | 36.00 |
| Example 177 | Shellac | 6.75 | 1,3-butanedio | 2.25 | Iron oxide pigment | 36.00 |
| Example 178 | Shellac | 6.75 | 1,3-butanedio | 3.15 | Iron oxide pigment | 35.10 |
| Example 179 | Shellac | 6.75 | 1,3-butanedio | 4.50 | Iron oxide pigment | 33.75 |
| Example 180 | Shellac | 6.75 | 1,3-butanedio | 6.75 | Iron oxide pigment | 31.50 |
| Example 181 | Shellac | 3.60 | Polyethylene glycol | 2.25 | Iron oxide pigment | 39.15 |
| Example 182 | Shellac | 3.60 | Polyethylene glycol | 3.15 | Iron oxide pigment | 38.25 |
| Example 183 | Shellac | 4.50 | Polyethylene glycol | 2.25 | Iron oxide pigment | 38/25 |
| Example 184 | Shellac | 4.50 | Polyethylene glycol | 3.15 | Iron oxide pigment | 37.35 |
| Example 185 | Shellac | 4.50 | Polyethylene glycol | 4.50 | Iron oxide pigment | 36.00 |
| Example 186 | Shellac | 6.75 | Polyethylene glycol | 2.25 | Iron oxide pigment | 36.00 |
| Example 187 | Shellac | 6.75 | Polyethylene glycol | 3.15 | Iron oxide pigment | 35.10 |
| Example 188 | Shellac | 6.75 | Polyethylene glycol | 4.50 | Iron oxide pigment | 33.75 |
| Example 189 | Shellac | 6.75 | Polyethylene glycol | 6.75 | Iron oxide pigment | 31.50 |
| Example 190 | Shellac | 3.60 | Dipropylene glycol | 2.25 | Iron oxide pigment | 39.15 |
| Example 191 | Shellac | 3.60 | Dipropylene glycol | 3.15 | Iron oxide pigment | 38.25 |
| Example 192 | Shellac | 4.50 | Dipropylene glycol | 2.25 | Iron oxide pigment | 38/25 |
| Example 193 | Shellac | 4.50 | Dipropylene glycol | 3.15 | Iron oxide pigment | 37.35 |
| Example 194 | Shellac | 4.50 | Dipropylene glycol | 4.50 | Iron oxide pigment | 36.00 |
| Example 195 | Shellac | 6.75 | Dipropylene glycol | 2.25 | Iron oxide pigment | 36.00 |
| Example 196 | Shellac | 6.75 | Dipropylene glycol | 3.15 | Iron oxide pigment | 35.10 |
| Example 197 | Shellac | 6.75 | Dipropylene glycol | 4.50 | Iron oxide pigment | 33.75 |
| Example 198 | Shellac | 6.75 | Dipropylene glycol | 6.75 | Iron oxide pigment | 31.50 |

TABLE 9

| | Step 1 | | | | | |
|---|---|---|---|---|---|---|
| | Polymer | | Plasticizer | | Pigment | |
| Example | Polyester | 3.60 | Dipropylene glycol | 2.25 | Organic pigment | 39.15 |
| Example | Polyester | 3.60 | Dipropylene glycol | 3.15 | Organic pigment | 38.25 |
| Example | Polyester | 4.50 | Dipropylene glycol | 2.25 | Organic pigment | 38.25 |
| Example | Polyester | 4.50 | Dipropylene glycol | 3.15 | Organic pigment | 37.35 |
| Example | Polyester | 4.50 | Dipropylene glycol | 4.50 | Organic pigment | 36.00 |
| Example | Polyester | 6.75 | Dipropylene glycol | 2.25 | Organic pigment | 36.00 |
| Example | Polyester | 6.75 | Dipropylene glycol | 3.15 | Organic pigment | 35.10 |
| Example | Polyester | 6.75 | Dipropylene glycol | 4.50 | Organic pigment | 33.75 |
| Example | Polyester | 6.75 | Dipropylene glycol | 6.75 | Organic pigment | 31.50 |

The use of the organic pigments could provide excellent color Clarity and strength and various and rich colors compared to the use of the inorganic pigments.

Examples 208 to 216

Preparation of Core Powders Consisting of Polyester Polymer-Plasticizer-Lake Dye Core powders were prepared in the same manner as Example 31, except that the acetone solvent used in step 1 of the preparation process of Example 31 was used to dissolve the plasticizer dipropylene glycol, a polyester polymer and a lake dye and that Yellow No. 5 lake, Red No. 230 lake or a mixture thereof was used as the lake dye. The specific kinds and contents of compounds used herein are shown in Table 10 below.

TABLE 10

| | Step 1 | | | | | |
|---|---|---|---|---|---|---|
| | Polymer | | Plasticizer | | Dye | |
| Example 208 | Polyester | 3.60 | Dipropylene glycol | 2.25 | Lake dye | 39.15 |
| Example 209 | Polyester | 3.60 | Dipropylene glycol | 3.15 | Lake dye | 38.25 |
| Example 210 | Polyester | 4.50 | Dipropylene glycol | 2.25 | Lake dye | 38.25 |
| Example 211 | Polyester | 4.50 | Dipropylene glycol | 3.15 | Lake dye | 37.35 |
| Example 212 | Polyester | 4.50 | Dipropylene glycol | 4.50 | Lake dye | 36.00 |
| Example 213 | Polyester | 6.75 | Dipropylene glycol | 2.25 | Lake dye | 36.00 |
| Example 214 | Polyester | 6.75 | Dipropylene glycol | 3.15 | Lake dye | 35.10 |
| Example 215 | Polyester | 6.75 | Dipropylene glycol | 4.50 | Lake dye | 33.75 |
| Example 216 | Polyester | 6.75 | Dipropylene glycol | 6.75 | Lake dye | 31.50 |

Even the use of the lake dye could provide a rich color.

Examples 217 to 225

Preparation of Core Powders Consisting of Polyester Polymer-Plasticizer-Natural Pigment Core powders were prepared in the same manner as Example 31, except that the acetone solvent used in step 1 of the preparation process of Example 31 was used to dissolve the plasticizer dipropylene glycol, the polyester polymer and a natural pigment and that turmeric, Gardenia, a graph skin pigment or a mixture of two or more thereof was used as the natural pigment. The specific kinds and contents of compounds used herein are shown in Table 11 below.

TABLE 11

| | Step 1 | | | | | |
|---|---|---|---|---|---|---|
| | Polymer | | Plasticizer | | Pigment | |
| Example 217 | Polyester | 3.60 | Dipropylene glycol | 2.25 | Natural pigment | 39.15 |
| Example 218 | Polyester | 3.60 | Dipropylene glycol | 3.15 | Natural pigment | 38.25 |
| Example 219 | Polyester | 4.50 | Dipropylene glycol | 2.25 | Natural pigment | 38.25 |
| Example 220 | Polyester | 4.50 | Dipropylene glycol | 3.15 | Natural pigment | 37.35 |
| Example 221 | Polyester | 4.50 | Dipropylene glycol | 4.50 | Natural pigment | 36.00 |
| Example 222 | Polyester | 6.75 | Dipropylene glycol | 2.25 | Natural pigment | 36.00 |
| Example 223 | Polyester | 6.75 | Dipropylene glycol | 3.15 | Natural pigment | 35.10 |
| Example 224 | Polyester | 6.75 | Dipropylene glycol | 4.50 | Natural pigment | 33.75 |
| Example 225 | Polyester | 6.75 | Dipropylene glycol | 6.75 | Natural pigment | 31.50 |

Even the use of the natural pigment provided the core particles having high brittleness in the same manner as the use of the iron oxide pigment.

Examples 226 to 242

Preparation of Capsule Powders Comprising Inorganic Material Coated on Core Powders Example 226

45 g of the core powder prepared in Example 31 was stirred and dispersed in a mixed solution of 207 ml of distilled water and 23 ml of ethanol at 25° C. for 10 minutes to make a solution. Meanwhile, 5 g of boron nitride and 50 g of titanium dioxide were stirred in 100 ml of distilled water at 25° C. for 10 minutes to make an inorganic suspension. Then, the inorganic suspension and the solution were mixed and stirred at 25° C. for 10 minutes, and the mixed solution was fed into an atomizer (rotating at a high speed of 10,000 rpm) at a constant rate of 120 ml/min using a metering pump. Herein, the mixed solution was fed into the atomizer at 160° C. and dried therein at 80° C. to obtain capsule powder. The obtained capsule powder had an outer diameter ranging from 10 μm to 150 μm.

Examples: 227 to 228

Capsules powders were prepared in the same manner as Example 226, except that the contents of titanium dioxide and boron nitride used to form the inorganic coating layer were changed. The specific kinds and contents of compounds used herein are shown in Table 12 below. The covering power of the inorganic coating layer according to its content is graphically shown in FIG. 16.

Examples 229 to 231

Capsule powders were prepared in the same manner as Example 226, except that varying amounts of titanium dioxide and zinc oxide were used to form an inorganic coating layer. The specific kinds and contents of compounds used herein are shown in Table 12 below. The covering power of the inorganic coating layer according to its content is graphically shown in FIG. 16.

Examples 232 to 234

Capsule powders were prepared in the same manner as Example 226, except that varying amounts of titanium dioxide, boron nitride and zinc oxide were used to form an inorganic coating layer. The specific kinds and contents of compounds used herein are shown in Table 12 below. The covering power of the inorganic coating layer according to its content is graphically shown in FIG. 16.

Examples 235 to 236

Capsule powders were prepared in the same manner as Example 226, except that varying amounts of titanium dioxide, boron nitride and talc were used to form an inorganic coating layer. The specific kinds and contents of compounds used herein are shown in Table 12 below. The covering power of the inorganic coating layer according to its content is graphically shown in FIG. 16.

Examples 237 to 239

Capsule powders were prepared in the same manner as Example 226, except that varying amounts of titanium dioxide, zinc oxide and talc were used to form an inorganic coating layer. The specific kinds and contents of compounds used herein are shown in Table 12 below. The covering power of the inorganic coating layer according to its content is graphically shown in FIG. 16.

Examples 240 to 242

Capsule powders were prepared in the same manner as Example 226, except that varying amounts of titanium dioxide, zinc oxide and mica were used to form an inorganic coating layer. The specific kinds and contents of compounds used herein are shown in Table 12 below. The covering power of the inorganic coating layer according to its content is graphically shown in FIG. 16.

TABLE 12

| | Step 2 | | | | |
|---|---|---|---|---|---|
| | Raw material | Core powder | Titanium dioxide | Boron nitride | |
| Example 226 | Content (%) | 45 | 50 | 5 | |
| Example 227 | Content (%) | 45 | 45 | 10 | |
| Example 228 | Content (%) | 45 | 40 | 15 | |
| | Raw material | Core powder | Titanium dioxide | Zinc oxide | |
| Example 229 | Content (%) | 45 | 50 | 5 | |
| Example 230 | Content (%) | 45 | 45 | 10 | |
| Example 231 | Content (%) | 45 | 40 | 15 | |
| | Raw material | Core powder | Titanium dioxide | Boron nitride | Zinc oxide |
| Example 232 | Content (%) | 45 | 30 | 5 | 20 |
| Example 233 | Content (%) | 45 | 35 | 5 | 15 |

TABLE 12-continued

| | | Step 2 | | | |
|---|---|---|---|---|---|
| Example 234 | Content (%) | 45 | 40 | 5 | 10 |

| Raw material | Core powder | Titanium dioxide | Boron nitride | Talc |
|---|---|---|---|---|
| Example 235 Content (%) | 45 | 40 | 5 | 10 |
| Example 236 Content (%) | 45 | 45 | 5 | 5 |

| Raw material | Core powder | Titanium dioxide | Boron nitride | Talc |
|---|---|---|---|---|
| Example 237 Content (%) | 45 | 30 | 15 | 10 |
| Example 238 Content (%) | 45 | 40 | 10 | 5 |
| Example 239 Content (%) | 45 | 40 | 5 | 10 |

| Raw material | Core powder | Titanium dioxide | Boron nitride | Mica |
|---|---|---|---|---|
| Example 240 Content (%) | 45 | 30 | 15 | 10 |
| Example 241 Content (%) | 45 | 40 | 10 | 5 |
| Example 242 Content (%) | 45 | 40 | 5 | 10 |

Figure 16:
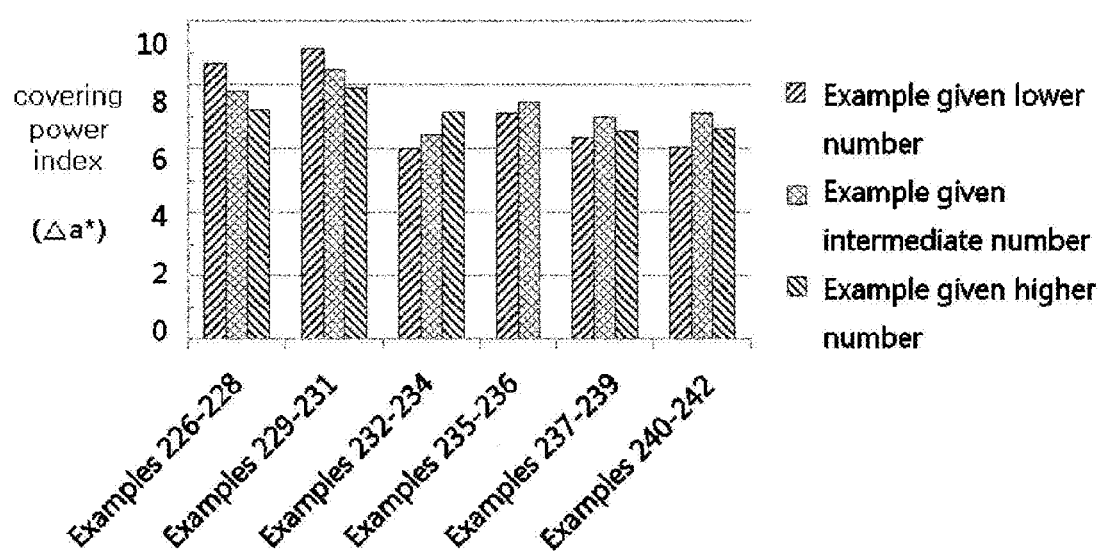
FIG. 16 is a graphic diagram showing the change in covering power according to the content of an inorganic coating layer in capsule particles of Examples 226 to 242.

As can be seen in FIG. 16, the step of forming the inorganic coating layer on the color capsule in Example 226 showed the effect of increasing the covering power of the color capsule.

In Examples 227 to 228, as the content of titanium dioxide constituting the inorganic coating layer of the color capsule increased, the covering power of the color capsule increased, and as the content of boron nitride increased, the covering power, feeling and gloss of the color capsule increased.

In Examples 229 to 231, titanium dioxide used as a white pigment increased the covering power of the color capsule while showing the SPF blocking ability (UVB region). Likewise, the use of zinc oxide, which has somewhat lower covering power compared to titanium dioxide, but has the ability to block SPF in other UV region (UVA), could increase the covering power of the color capsule while providing color capsules capable of blocking light in the UV AB regions.

In Examples 232 to 234, the effects of Examples 227 to 231 could be expected, and the case having the highest content of titanium dioxide showed the highest covering power.

In Examples 235 to 236, the same effects as those of Examples 227 to 228 could be obtained, and talc was added in order to increase the feeling improvement effect which can be obtained using boron nitride. This feeling improvement effect was further increased as the content of talc increased.

In Examples 237 to 239, the same effects as those of Examples 229 to 231 could be obtained, and the feeling improvement effect could be obtained using talc in place of boron nitride.

In Examples 240 to 242, the same effects as those of Examples 229 to 231 could be obtained, and the feeling improvement effect could be obtained using mica in place of boron nitride or talc. As the content of mica increased, the feeling of the color capsules was further improved.

Examples 243 to 245

Preparation of Cosmetic Compositions Containing Color Capsules

Example 243

Preparation of W/O Emulsion Cream Emulsion Containing Color Capsules 4.56 g of the coated color capsules prepared in Example 226 were added to and mixed with 95.44 g of a W/O cream based composition, thereby preparing cream. The specific components and contents of the W/O cream base composition are shown in Table 13 below.

TABLE 13

| WO emulsion formulation | |
|---|---|
| Components | Contents (parts by weight) |
| KF-6033 | 2.00 |
| Tegosoft CT | 3.00 |
| TIO2 CR50 OTS | 4.50 |
| Mica SDM | 1.50 |
| Perfomalene 400 | 0.30 |
| Ozokerite | 0.50 |
| Abil WE-09 | 4.00 |
| LP/Phytosqualane/Nexbase 2006 | 3.00 |
| CEH | 5.00 |
| Vit E acetate | 0.20 |
| Bentongel GTCC V | 6.00 |
| BSG 250/Puresil CM | 2.00 |
| SF0015Z/DC 345 | 6.00 |
| MP | 0.20 |
| 1,3 BG (80° C.) | 1.00 |
| $MGSO_4 7H_2O$ | 1.20 |
| EDTA-2NA | 0.04 |
| Elestab CPN (chlorphenesin) | 0.15 |
| 1,3 BG | 5.00 |
| Glycerin | 3.00 |
| Keltrol F | 0.06 |
| DI-water | 46.79 |
| FeO (Yellow) | 3.50 |
| FeO (Red) | 0.80 |
| FeO (Black) | 0.26 |
| Total | 100 |

Example 244

Preparation of W/O Emulsion Cream Containing Color Capsules 4.56 g of the coated color capsules prepared in Example 226 were added to and mixed with 95.44 g of a W/S cream base composition, thereby preparing cream. The specific components and contents of the W/S cream base composition are shown in Table 14 below.

TABLE 14

| W/S emulsion formulation | |
|---|---|
| Components | Contents (parts by weight) |
| KF-6028 | 2.00 |
| SF0015Z/DC345 | 3.00 |
| TiO2 CR50 OTS | 4.00 |
| Mica SDM | 1.50 |
| Abil wax 9801 | 1.00 |
| Abil EM-90 | 2.00 |
| DC 9040 | 4.00 |
| Sf0015Z/DC345 | 5.00 |
| KF56/DC556/SF5600 | 3.00 |
| DC200F 16cs/SF1000N-20 | 4.00 |
| Bentongel VS 5 PCV | 6.00 |
| MP | 0.20 |
| 1,3 BG (80° C.) | 1.00 |
| NaCl | 1.50 |
| EDTA-2Na | 0.02 |
| Elestab CPN (chlorphenesin) | 0.15 |
| 1,3 BG | 5.00 |
| Glycerin | 3.00 |
| DI-water | 47.07 |
| 1% Na-Hyaluronate | 2.00 |
| FeO (Yellow) | 3.50 |

TABLE 14-continued

| W/S emulsion formulation | |
|---|---|
| Components | Contents (parts by weight) |
| FeO (Red) | 0.80 |
| FeO (Black) | 0.26 |
| Total | 100.00 |

Example 245

Preparation of O/W Emulsion Cream Formulation Containing Color Capsules 4.56 g of the coated color capsules prepared in Example 226 were added to and mixed with 95.44 g of an 0/W cream base composition, thereby preparing cream. The specific components and contents of the W/O cream base composition are shown in Table 15 below.

TABLE 15

| O/W emulsion formulation | |
|---|---|
| Components | Contents (parts by weight) |
| CETOS KD | 1.50 |
| GMS 105 | 1.50 |
| Arlacel #165 | 1.50 |
| Tween #60 | 1.00 |
| Arl #83 | 0.50 |
| D-M | 0.10 |
| D-P | 0.10 |
| Phytosqualane | 3.00 |
| Puresyn 4 | 3.00 |
| DC200 100 cs | 0.50 |
| DI-Water | 77.24 |
| 1,3 BG | 5.00 |
| Sepiplus #400 | 0.50 |
| FeO (Yellow) | 3.50 |
| FeO (Red) | 0.80 |
| FeO (Black) | 0.26 |
| Total | 100.00 |

Measurement of Color Coordinates of Particles

The color coordinates of each of the cream formulations prepared in Examples 243, 244 and 245 were measured, and the results of the measurement are shown in Table 16 below.

TABLE 16

| | Color coordinates | | |
|---|---|---|---|
| | L* | a* | b* |
| Example 243 (W/O emulsion formulation) | 74.866 | 13.958 | 31.359 |
| Example 244 (W/S emulsion formulation) | 73.872 | 14.914 | 32.540 |
| Example 245 (O/W emulsion formulation) | 63.549 | 13.231 | 30.479 |

As can be seen in Table 16 above, the color capsules prepared according to the present invention showed similar color coordinates in the above formulations (the reason why the lightness of the O/W emulsion formulation was low because no $TiO_2$ was used in the base cream), suggesting that the color capsules can be stably used in all formulations. This indicates that the prevent invention solves the problem in that, because the swelling properties of capsules differ between emulsion formulations, the color expressed when the capsules particles break differs between the emulsion formulations.

According to the present invention, the above-described problems occurring during the preparation of the color capsule particles can be solved, and a color cosmetic composition having improved unique properties, such as improved color coordinates and covering power, can be obtained.

As described above, in the color capsule composition of the present invention, the polymer and the plasticizer that swells the polymer are used such that the capsules easily break under specific conditions. Porosity can be imparted to the capsule particles using a simple spray dryer so as to boost the effects of the capsule particles.

Also, according to the present invention, core-shell particles having covering power can be prepared by simply forming on the outer wall of the core a coating layer of carbon dioxide, boron nitride, etc., which have covering power.

Moreover, according to the present invention, because no surfactant is used during the formation of the capsule particles, the physical properties of the final product can be easily controlled, and thus the number of additional process steps can be reduced. When the spray dryer is used, a drying process can be performed at the same time as the particle-forming process, and thus no wastewater is generated, thus reducing the production cost.

Furthermore, because the closed spray-drying system is used, a volatile solvent that is generated during the drying process can be recycled without being discharged, and the preparation process is environmentally friendly.

Meanwhile, color capsules containing natural or synthetic organic or inorganic pigments can be prepared which can express a wide range of colors.

In addition, the color capsules prepared according to the present invention can be used to prepare W/O emulsion formulations, W/S emulsion formulations and O/W emulsion formulations.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A method for preparing a color capsule composition for cosmetics, the method comprising the steps of:
uniformly mixing a color pigment, a plasticizer and a polymer in a first solvent to produce a first mixture solution, wherein the polymer and the plasticizer are dissolved in the first solvent by stirring at 25° C. to prepare a solution, meanwhile the color pigment is dispersed in the first solvent at 25° C. to prepare a dispersion of the color pigment in the first solvent, and the solution is mixed with and uniformly dispersed in the dispersion at the same temperature, so as to produce the first mixture solution;
spray-drying the first mixture solution to produce core particles in which the color pigment is covered by the polymer;
uniformly mixing the obtained core particles, a functional pigment and a second solvent to produce a second mixture, wherein the functional pigment is stirred in the second solvent at 25° to obtain an inorganic suspension of the functional pigment in the second solvent, the obtained core powder is dispersed by stirring in the second solvent at 25° C., and the inorganic suspension and the dispersed core powder are mixed with each other stirring at 25° C.; and spray-drying the second mixture to produce capsule particles, in each of which a coating layer of the functional pigment is formed on the outer surface of the polymer,
wherein, in the step of producing the first mixture solution, the polymer, the color pigment and the plasticizer are used in amounts of 5-15 wt %, 70-90 wt % and 5-15 wt %, respectively, based on the total weight of the polymer, the color pigment and the plasticizer, and in the step of producing the second mixture, the core particles and the functional pigment are used in amounts of 80-40 wt % and 20-61) wt %, respectively, based on the total weight of the core particles and the functional pigment, wherein each of the first and second solvents consists of distilled water.

2. The method of claim 1, wherein the polymer is any one selected from the group consisting of polyester, a polyester emulsion, polyaminomethacrylate, polyvinylpyrrolidone, hydroxypropylmethylcellulose, and shellac.

3. The method of claim 1, wherein the plasticizer is any one selected from the group consisting of 1,3-butanediol, polyethylene glycol, dipropylene glycol, and a mixture of two or more thereof.

4. The method of claim 1, wherein the color pigment is any one selected from the group consisting of iron oxide pigments, organic pigments, lake dyes, and natural pigments.

5. The method of claim 1, wherein fatty acid is further added to the first mixture solution.

6. The method of claim 5, wherein the fatty acid is any one selected from the group consisting of stearic acid, palmitic acid, oleic acid, linoleic acid, and linolenic acid.

7. The method of claim 1, wherein the functional pigment is any one selected from the group consisting of titanium dioxide, zinc oxide, boron nitride, talc, mica, and a mixture of two or more thereof.

8. The method of claim 1, further comprising a step of sieve-screening dried core particles right after the step of spray-drying the first mixture solution, and a step of sieve-screening dried capsule particles right after the step of spray-drying the second mixture solution.

* * * * *